(12) United States Patent
Lee

(10) Patent No.: US 7,745,117 B2
(45) Date of Patent: Jun. 29, 2010

(54) METHODS FOR INCORPORATING NON-PERFECTLY MATCHED OLIGONUCLEOTIDES INTO TARGET-SPECIFIC HYBRIDIZATION SEQUENCES

(75) Inventor: Inhan Lee, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1069 days.

(21) Appl. No.: 10/862,662

(22) Filed: Jun. 7, 2004

(65) Prior Publication Data

US 2005/0064457 A1   Mar. 24, 2005

Related U.S. Application Data

(60) Provisional application No. 60/476,382, filed on Jun. 6, 2003.

(51) Int. Cl.
*C12Q 1/68* (2006.01)
*C07H 21/02* (2006.01)
*C07H 21/04* (2006.01)

(52) U.S. Cl. ............................ 435/6; 536/23.1; 536/24.3
(58) Field of Classification Search ...................... 435/6; 536/23.1, 24.3
See application file for complete search history.

(56) References Cited

U.S. PATENT DOCUMENTS

| | | | | |
|---|---|---|---|---|
| 5,556,749 | A * | 9/1996 | Mitsuhashi et al. | 435/6 |
| 5,639,612 | A * | 6/1997 | Mitsuhashi et al. | 435/6 |
| 5,985,599 | A * | 11/1999 | McKenzie et al. | 435/69.1 |
| 6,312,902 | B1 | 11/2001 | Shultz et al. | |
| 6,461,816 | B1 * | 10/2002 | Wolber et al. | 435/6 |

FOREIGN PATENT DOCUMENTS

| | | |
|---|---|---|
| EP | 1 280 090 A1 | 1/2003 |
| JP | 2004024247 | 1/2004 |
| WO | WO 97/46711 | 12/1997 |
| WO | WO 03/044228 A1 | 5/2003 |

OTHER PUBLICATIONS

"Software to Determine Optimal Oligonucleotide Sequences Based on Hybridization Simulation Date", D. Hyndman et al., Product Application Focus, vol. 20, pp. 1090-1097, Jun. 1996.
"Enhanced Discrimination of Single Nucleotide Polymorphisms by Artificial Mismatch Hybridization", Zhen Guo et al., Nature Biotechnology, vol. 15, pp. 331-335, Apr. 1997.
"Spreadsheet Software for Thermodynamic Melting Point Prediction of Oligonucleotide Hubridization with and without Mismatches", Ekkehard Schutz et al., Biotechniques, vol. 27, No. 6, Dec. 1999.
"Mutation Detection by Stacking Hybridization on Genosensor Arrays", Rogelio Maldonado-Rodriguez et al., Molecular Biotechnology, vol. 11, pp. 13-25, 1999.
"Selection of Optimal DNA Oligos for Gene Expression Arrays", Fugen Li et al., Bioinformatics, vol. 17, No. 112001, pp. 1067-1076, Nov. 2001.

* cited by examiner

*Primary Examiner*—Stephen Kapushoc
*Assistant Examiner*—Narayan K Bhat
(74) *Attorney, Agent, or Firm*—Brooks Kushman P.C.

(57) ABSTRACT

The present invention provides a method of designing target-specific hybridization sequences which include one or more mutations. The method of the invention comprises selecting a candidate target nucleotide sequence in a subject nucleotide sequence. A first complementary nucleotide sequence to the target nucleotide sequence is identified by applying the known bonding relationships of the nucleotides. Next, a second complementary nucleotide sequence having one or more mutations is constructed. The amount of the "target-second complementary nucleotide sequence" hybrid formed when the candidate target nucleotide sequence and second complementary nucleotide sequences are combined in the presence of interfering sequences is characterized and used to assess utility of the second complementary nucleotide sequence. The present invention also provides the target-specific hybridization sequences designed by the methods of the invention.

19 Claims, 12 Drawing Sheets

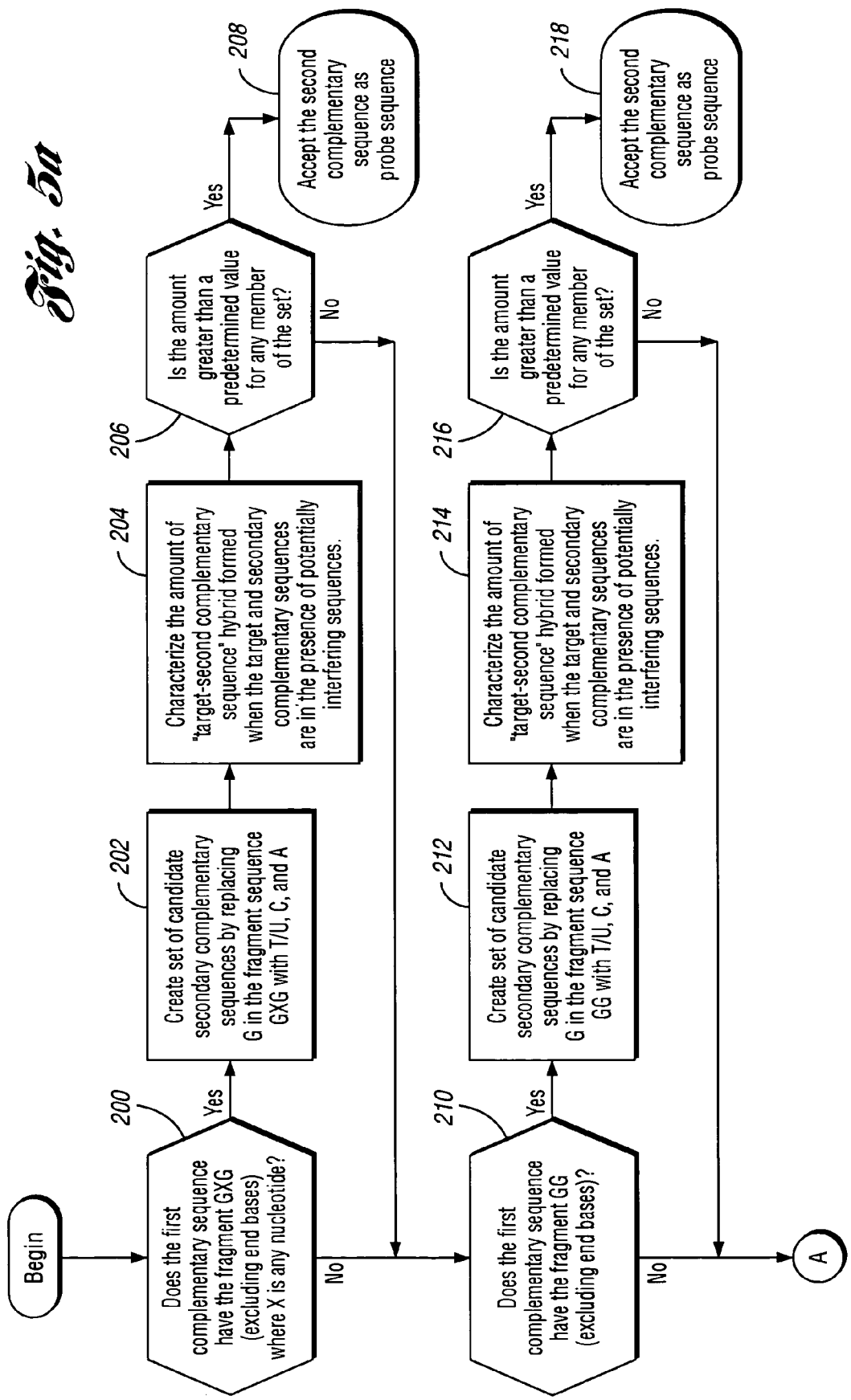

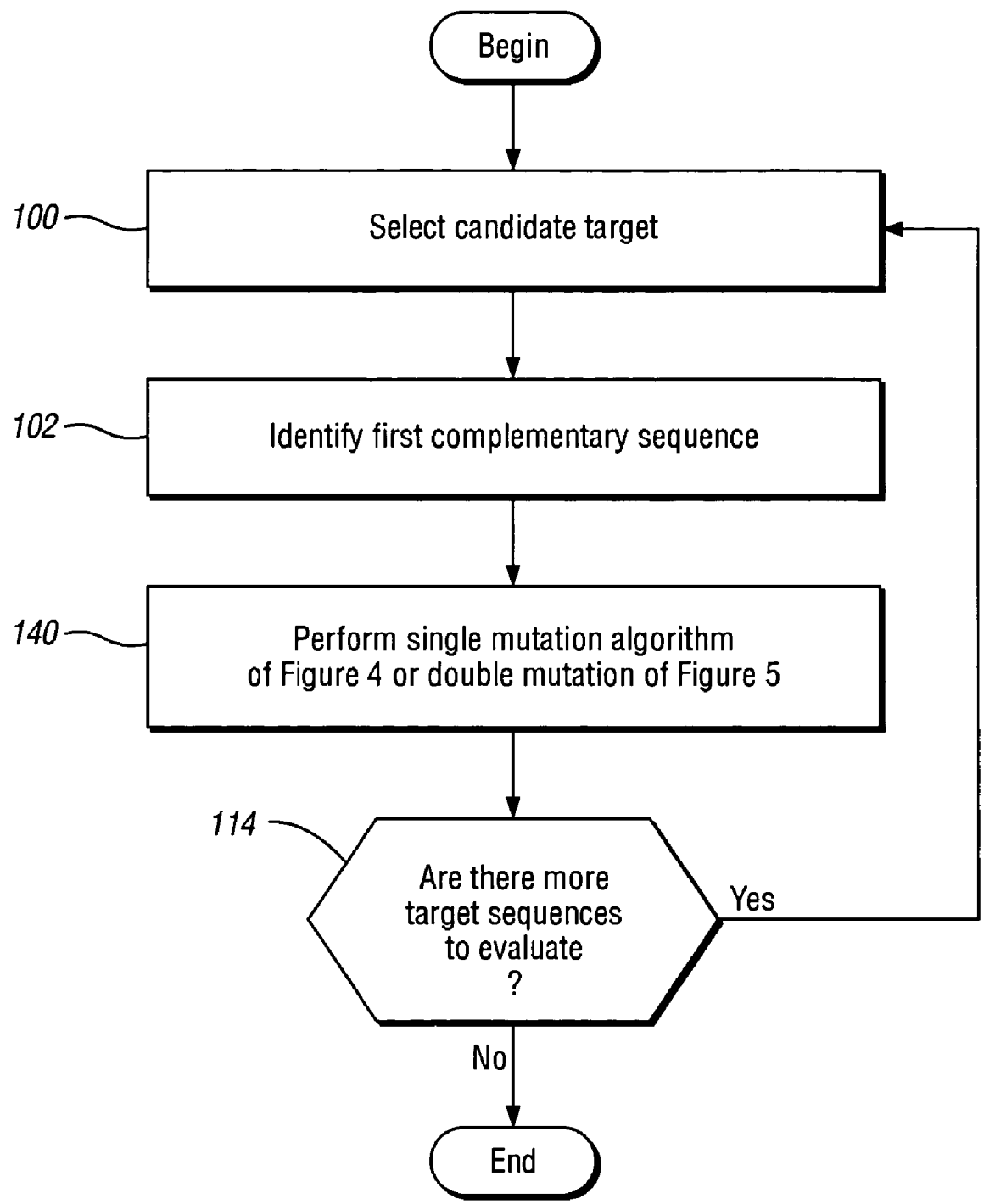

SEQUENCE LISTING

<160> NUMBER OF SEQ ID NOS: 13

<210> SEQ ID NO 1
<211> LENGTH: 60
<212> TYPE: DNA
<213> ORGANISM: unknown
<220> FEATURE:
<223> OTHER INFORMATION: This is an example about how nucleotide
      sequences are symbolically coded.
<220> FEATURE:
<221> NAME/KEY: DDD
<222> LOCATION: (1)..(60)
<223> OTHER INFORMATION: STUGG

<400> SEQUENCE: 1
cccgtaccac agcatgctct actactacgg ccaaatccac atatacgaac aggatggagg      60

<210> SEQ ID NO 2
<211> LENGTH: 60
<212> TYPE: DNA
<213> ORGANISM: Homo sapiens

<400> SEQUENCE: 2
caggccatag agaagaggga tcacatcgtg gagatgcagc tgaggcagca caaggagagc      60

<210> SEQ ID NO 3
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 3
caggccatag agaagacgga tcacatcgtt gagatgcagc tgagtcagca caaggagagc      60

<210> SEQ ID NO 4
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 4
cacagagcac gcttgcatct gactgaccca ccattacacc cacagacttc acaagcccta      60

<210> SEQ ID NO 5
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 5
catccgcaaa gggagagacc actatgccta ctcctactac ccgaaaccgg tgaacatgac      60

<210> SEQ ID NO 6
<211> LENGTH: 60
<212> TYPE: DNA
<213> ORGANISM: Artificial

```
<220> FEATURE:
<223> OTHER INFORMATION: This is a complementary sequence to a human
      mRNA sequence having several point mutations.

<400> SEQUENCE: 6
ctgtgggctg tttagtgcca tgcacccttt acagtgtgtc ctccaattgc agaggtctct      60

<210> SEQ ID NO 7
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 7
gcgatggtgt gaagaaaaga aagtccattt ccagcgttca gttaatggaa tcctcagaga      60

<210> SEQ ID NO 8
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 8
gtgggatact agcgtgtcca cattgtcctt tgataatgag aagtcatcct cgagcacagc      60

<210> SEQ ID NO 9
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 9
tatggtacag gactgtcaac gaaacctagc acggctcttg cttccggtct tcagaatgcc      60

<210> SEQ ID NO 10
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 10
ctcaagaatc ccagtgtgtg tgtagcctcc acagaaaggt cgttttctcg gagtccagag      60

<210> SEQ ID NO 11
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 11
tcctcatact gcctacagag tgcctagcac ttgggacttc cataaaggat gagcctgggg      60

<210> SEQ ID NO 12
<211> LENGTH: 60
<212> TYPE: DNA
<213> ORGANISM: Artificial
```

-continued

```
<220> FEATURE:
<223> OTHER INFORMATION: This is a complementary sequence to a human
      mRNA sequence having several point mutations.

<400> SEQUENCE: 12
gacgaggaga ctatctcacc cagggtggtc cgacggcggg tcttcctgaa gcggaatgag      60

<210> SEQ ID NO 13
<211> LENGTH: 60
<212> TYPE: DNA
<213> ORGANISM: Artificial
<220> FEATURE:
<223> OTHER INFORMATION: This is a complementary sequence to a human
      mRNA sequence having several point mutations.

<400> SEQUENCE: 13
cccgtaccac agcatgctct actactacgg ccaaatccac atatacgaac aggatggagg      60
```

METHODS FOR INCORPORATING NON-PERFECTLY MATCHED OLIGONUCLEOTIDES INTO TARGET-SPECIFIC HYBRIDIZATION SEQUENCES

CROSS-REFERENCE TO RELATED APPLICATIONS

This application claims the benefit of U.S. Provisional Application Ser. No. 60/476,382 filed Jun. 6, 2003, the entire disclosure of which is hereby incorporated by reference.

BACKGROUND OF THE INVENTION

1. Field of the Invention

The present invention is related to methods for developing target-specific hybridization sequences, and in particular, to a method for developing hybridization probes using natural nucleotide mismatches and having reduced cross hybridization.

2. Background Art

The ability of DNA microarrays to analyze tens of thousands of genes in one assay has led to continuous improvements in microarray techniques and to software that analyzes microarray data. While researchers have begun to pay close attention to the quality of microarray data, the problem of cross-hybridization has received little consideration.

The success of microarrays in gene expression profiling depends on the specificity between the selected probes and the target genes. All DNA microarrays operate on the principle of DNA hybridization between complementary target and probe sequences. In cross-hybridization, an expressed gene hybridizes with probes designed for other genes as well as with its own designated probe, introducing noise. Experiments with cDNA microarrays have raised cross-hybridization concerns. Although oligonucleotides have the advantage of greater specificity than cDNA microarrays, they too are subject to some degree of cross-hybridization. In particular, genes of highly similar sequences such as those in a large gene family are very difficult to distinguish in microarray experiments.

An even greater problem related to cross-hybridization arises when microarrays are employed to discriminate single nucleotide polymorphism ("SNPs"). In order to enhance specificity, new probes other than conventional linear oligonucleotides have been developed, such as structured DNA probes (molecular beacons) or gold nanoparticle probes. Another approach includes the preparation of target genes by pooling two separate PCRs. Unfortunately, all of these approaches require new materials and/or complex processes. A simpler, more promising approach by Guo et al. involves the introduction of artificial mismatches in the probes to enhance the discrimination of SNPs. However, they introduced artificial nucleotides, which cannot utilize the hybridization differences between natural nucleotides, for mismatch pairs. Moreover, such artificially nucleotides are not appropriate for in vivo applications. Also their dataset was limited in size and only short length oligos were used in the experiments. Moreover, it is difficult to extend their findings to general SNP probe selection.

Accordingly, there is a need in the prior art for systematic methods of designing target-specific hybridization sequences with little or no cross-hybridization.

SUMMARY OF THE INVENTION

The present invention solves one or more problems of the prior art by providing in one embodiment a method of designing a target-specific hybridization sequence. In implementing the method of the invention, one or more target-specific hybridization sequences are identified each of which includes one or more mutations in which a nucleotide is replaced such that the target-specific hybridization sequence is not complementary at the position of the mutation. Accordingly, the target-specific hybridization sequences identified by the method of the invention are imperfect complementary sequences to an identified target. The method of the invention is advantageously implemented on a microprocessor and comprises selecting a candidate target nucleotide sequence in a subject nucleotide sequence. A first complementary nucleotide sequence to the target nucleotide sequence is identified by applying the known bonding relationships of the nucleotides. Next, a second complementary nucleotide sequence having one or more mutations is constructed. The amount of "target-second complementary nucleotide sequence" hybrid formed when the candidate target nucleotide sequence and second complementary nucleotide sequences are combined in the presence of interfering sequences is characterized. If the amount of "target-second complementary nucleotide sequence" hybrid is greater than a predetermined value, the second complementary nucleotide sequence is identified as a symbolic representation for the target-specific hybridization sequence.

In another embodiment of the present invention, a target-specific hybridization sequence is provided. The target-specific hybridization sequence is demonstrated as having improved discrimination performance by the methods set forth above. The target-specific hybridization sequence of the invention includes a sequence of nucleotides that are complementary to a target nucleotide sequence except for the occurrence of one or more mutations at selected positions $P_n$.

The methods of the invention are advantageously used to design target-specific hybridization sequences that are useful in a multitude of applications. For example, the symbolic representation of the target-specific hybridization sequence identified by the methods of the invention may be used to generate an actual nucleotide sequence that is incorporated in probes that are used in assay and in particular DNA microarrays. The superior discriminations of the target-specific hybridization sequence of the invention allows such assays to function with decreased noise by cross hybridization. Moreover, assays developed by the methods of the invention may also be used in the development of drugs and drug therapies by providing assays that can evaluate gene expression from a mammal treated with a drug. In other applications, the symbolic representation of the target-specific hybridization sequence identified by the methods of the invention may be used to generate an actual nucleotide sequence that can be incorporated into drugs that activate certain genes or act as the initiators in PCR applications. A similar application of these target-specific hybridization sequences would be to incorporate them into single or double stranded RNA (dsRNA). In dsRNA applications, either the sense or antisense sequences of the dsRNA may be the target-specific hybridization sequence designed by the methods of the invention.

BRIEF DESCRIPTION OF THE DRAWINGS

FIG. 6 is a flowchart illustrating the incorporation of mutations of FIGS. 4 and 5 into the method of the present invention;

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

Figure 1:
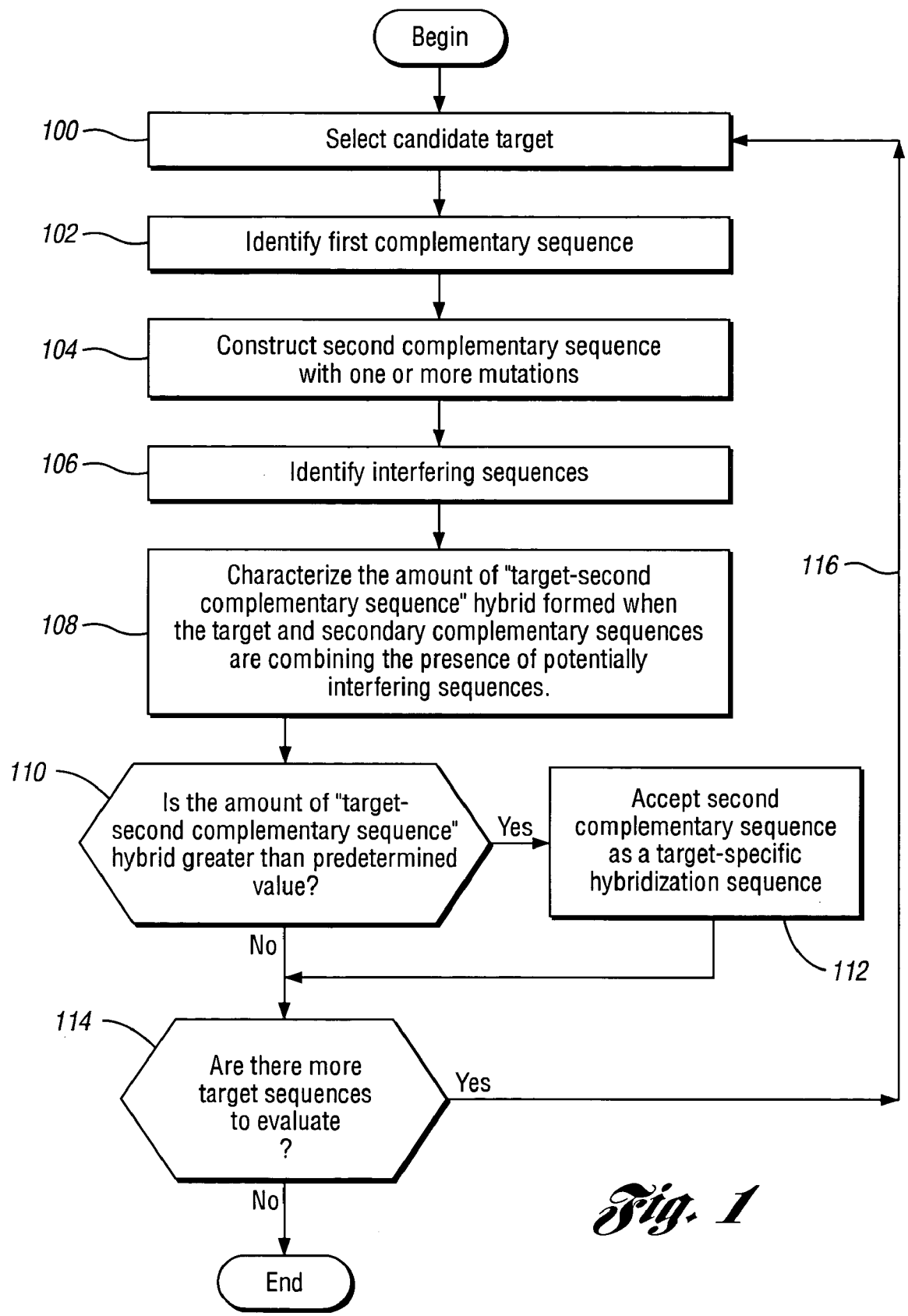
FIG. 1 is a flowchart illustrating the method of the present invention.

In an embodiment of the present invention, a method of designing a target-specific hybridization sequence is provided. With reference to FIG. 1, a flowchart summarizing this first embodiment is provided. The method comprises selecting a (symbolic representation of a) candidate target nucleotide sequence in a subject nucleotide sequence as set forth in block 100. The term "subject nucleotide sequence" as used herein means any nucleotide sequence for which there is a need or desire for developing the target specific hybridization sequence. The subject nucleotide sequence may be an entire genome or part of a genome, transcribed and reversed transcribed sequences (i.e., mRNA, 5'-UTR, 3'-UTR, cDNA), dsRNA, single or double stranded DNA, and the like. Typically, the subject nucleotide sequence has a length that is equal to or greater than the candidate target nucleotide sequence (usually much longer). The method of the invention is typically implemented by a microprocessor executing a series of programming commands. Virtually any programming language may be used for producing codes that implement the methods of the invention (C, C++, Perl, Fortran, Visual Basic, and the like.) Since the length of the subject nucleotide sequence may be quite high, this sequence is typically stored on a computer storage medium—CDROM, hard drives, floppy drive, and the like. Also, such subject nucleotide-sequence may be downloaded from various internet sites and databases. While operating on the subject nucleotide sequence, portions of or the entire nucleotide sequence are loaded into memory so that the microprocessor may manipulate them in accordance to the steps of the method of the invention. A (symbolic representation of a) first complementary nucleotide sequence to the target nucleotide sequence is identified (Block 102). Next, a (symbolic representation of a) second complementary nucleotide sequence having one or more mutations is constructed (Block 104). This is accomplished by replacing nucleotides at each of selected positions $P_n$ in the first complementary nucleotide sequence to form the second complementary nucleotide sequence. Accordingly, the second complementary nucleotide sequence is not perfectly matched and has a mismatch at each of selected positions $P_n$ when the second complementary nucleotide sequence is hybridized with the candidate target nucleotide sequence. In some variations of the present invention, the candidate target nucleotide sequence will not be significantly self-complementary thereby having little tendency to form secondary structure by the candidate target nucleotide sequence folding onto itself. In other variations of the present invention, the requirement that the first complementary nucleotide sequence not be self-complementary is relaxed. Typically, natural nucleotides are used to construct the complementary nucleotide sequences. Such nucleotides comprise the following bases: adenine, guanine, cytosine, thymine, and uracil. When nucleotides are being referred to herein, "A" refers to a nucleotide containing adenine, "G" refers to a nucleotide containing guanine, "C" refers to a nucleotide containing cytosine, "T" refers to a nucleotide containing thymine, and "U" refers to a nucleotide containing uracil. For such nucleotides, the natural pairings are A-T and C-G for DNA and A-U and C-G for RNA. These are the pairings that are used to construct perfectly complementary sequences. It should be obvious that target nucleotide sequences, first complementary nucleotide sequences, second complementary nucleotide sequences, target-specific hybridization sequence, and any other nucleotide sequence or fragment mentioned, herein refers to symbolic representations of these sequences (or fragments) that may be manipulated by the microprocessor in executing the methods of the invention unless the context or language make it clear that the actual physical nucleotide sequence is being referred to. If the word "actual" precedes a sequence the actual physical sequence is being referred to. Similarly, for added clarity, a sequence may be described as a symbolic representation. For example, such a sequence may be represented textually by a sequence such as (SEQ ID NO 1) CCCGTACCACAGCAT-GCTCTACTACTACGGCCAAATCCA-CATATACGAACAG GATGGAGG. Any type of coding for the sequences may be used (binary, alphanumeric, hex) so long as it is interpretable by the microprocessor.

Still referring to FIG. 1, one or more (symbolic representations of) interfering nucleotide sequences may optionally be identified (Block 106). The interfering nucleotide sequences have at least a predetermined number of sequential nucleotides in common with the second complementary nucleotide sequence and therefore may cross hybridize with the candidate target nucleotide sequences. Typically, the interfering nucleotide sequence will have at least 14 sequential nucleotides in common with the second complementary nucleotide sequences. Alternatively, the interfering nucleotide sequence will have at least 90% of its nucleotides in common with the second complementary nucleotide sequences. As illustrated in Block 108, the amount of "target-second complementary nucleotide sequence" hybrid formed when the target and second complementary nucleotide sequences are combined in the presence of the interfering sequences is characterized (Block 110). If the amount of the "target-second complementary nucleotide sequence" hybrid is greater than a predetermined value, the second complementary nucleotide sequence is identified as a symbolic representation of the target-specific hybridization sequence (Block 112). In a variation of the invention, the amount of the "target-second complementary nucleotide sequence" hybrid is determined by calculating the differences between a hybridization function for a "target-second complementary nucleotide sequence" hybrid and an "interfering sequences-second complementary sequence" hybrid. If the differences are such that the amount of the "target-second complementary nucleotide sequence" hybrid is greater than the predetermined value, the second complementary nucleotide sequence is identified as the target-specific hybridization sequence. Such a hybridization function provides quantification of the amount of hybridization. Suitable hybridization functions include, for example, the melt temperature ("$T_m$"), the difference in Gibbs free energy, interaction energy, and the percent hybridization. Interaction energy as used herein refers to any measurement of the bonding or attraction between the two strands of a hybridized sequence. If the differences between melt temperature is used, the predetermined value is typically about 10° C. or the melt temperature of the "interfering sequences-second complementary nucleotide sequence" hybrid 5° C. below the experimental assay temperature (especially for target-second complementary nucleotide sequence" hybrid melt temperatures of about 80° C.)

Selection of the melt temperature as the hybridization function is particularly suitable since the thermodynamics of nucleic acid hybridization are well established and generally accepted in predicting melting temperature. The $T_m$ of two-nucleotide hybridizations can be obtained from several public websites as well as calculated using either nearest neighbor thermodynamics or the simple % GC-content method. The thermodynamic parameters of single base pair mismatches have also been determined experimentally. Nearest neighbor calculations are known to predict experimental results well. By definition, thermodynamic parameters depend on the sequence content of nearest neighbor, 5'/3' direction, and the chain terminal sequences, but not on the position of oligonucleotides. A longer oligo is thought to have higher calculated $T_m$ because of the additive calculations for enthalpy and entropy changes. However, it is much faster computationally to consider one sequence at a time instead of two consecutive sequences, which include directional information. The $T_m$ of an oligonucleotide bound to a complementary nucleotide is the temperature at which 50% of duplex strands are separated. Since it is at equilibrium and the reaction is intermolecular, $T_m$ depends on oligonucleotide concentration as well as $Na^+$ concentration. A nearest neighbor model may calculate $T_m$ from the following equation:

$$T_m = T° \cdot \Delta H°/(\Delta H° - \Delta G° + R \cdot T° \ln[C/4]) + 16.6 \cdot \log_{10}\{[Na^+]/(1+0.7[Na^+])\} - 269.3 \qquad 1$$

where $\Delta G°$ is the standard free energy, $\Delta H°$ the enthalpy, $T°$ the temperature, R the gas constant (1.987 cal/kmol), and C the total oligonucleotide concentration for non-self-complementary cases if the strands are in equal concentration. $\Delta G°$ and $\Delta H°$ are for the sums of all nearest neighbor and chain end contributions in coil-to-helix transition. At $Na^+$ concentration of 1 M, equation 1 becomes:

$$T_m = \Delta H°/(\Delta S° + R \ln[C/4]) \qquad 2$$

where $\Delta S°$ is the predicted entropy change. C/4 becomes C for self-complementary oligonucleotide duplexes. We used equation 2 for $T_m$ calculations with the thermodynamic parameters in the table in the Supplementary Material set forth below. Since the parameters for the mismatched pairs are not applicable to terminal or penultimate position, we did not calculate mismatch pairs for those positions with this method. $T_m$ calculations may be performed using a number of commercially available software packages. A useful software package is the OMP software package (DNA Software, Inc., Ann Arbor, Mich.; http://www.dna-software.com). This software simulates and predicts nucleic acid hybridization in solution and produces structural and thermodynamic parameters. OMP predicts nucleotide acid structures utilizing dynamic programming methods and calculates their reactions in equilibrium based on nearest neighbor calculations, which determine 'thermal' $T_m$ using equation 2. OMP calculates 'actual' $T_m$ considering competing secondary structures of oligonucleotides. Moreover, since the OMP software is capable of running in a command line mode, integration into a computer program executing the steps of the methods of the invention is easy.

As shown in decision block 110, if the amount of the "target-second complementary nucleotide sequence" hybrid is not greater than a predetermined value or if more potential target-specific hybridization sequences are desired, a determination is made as to whether or not additional candidate target nucleotide sequences are to be evaluated (block 114). If additional sequences are to be evaluated, the candidate target nucleotide sequence is replaced with an alternative candidate target nucleotide sequence as indicated by loop 116. Moreover, this process may be repeated for any desired number of candidate sequences until a desired number of potential target-specific hybridization sequences are identified.

Figure 2:
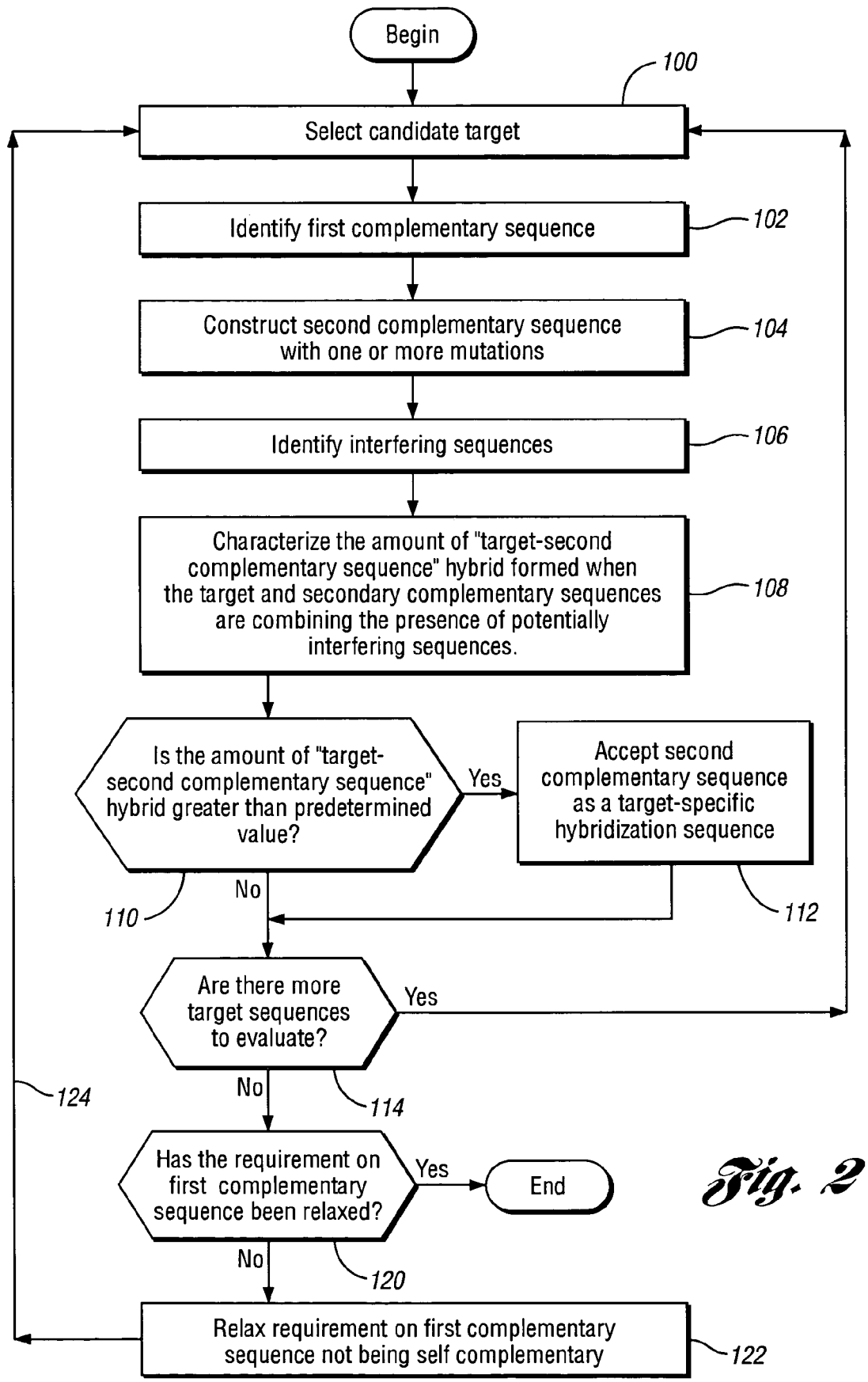
FIG. 2 is a flowchart illustrating the method of the present invention in which the restriction on the first complementary nucleotide sequence being non-self complementary may be relaxed.

With reference to FIG. 2, a flowchart illustrating a variation of the present invention is provided. In this variation a set of candidate target nucleotide sequences are evaluated using the method set forth in FIG. 1 with the requirement that each target nucleotide sequence not be self-complementary. If the method fails to identify a desired number of target-specific hybridization sequences the requirement of not being self-complementary is removed thereby allowing these additional candidate target nucleotide sequences to be evaluated. Accordingly, subject to these conditions, blocks 100 to 114 are the same as those set forth above for FIG. 1. After every desired target that is not self-complementary is evaluated, the condition of not being self-complementary may be relaxed as indicated in decision block 120. If the condition has already been relaxed and all candidate sequences evaluate the algorithm ends (block 122). If the condition has not been relaxed, the condition is relaxed as indicated in loop 124.

Figure 3:
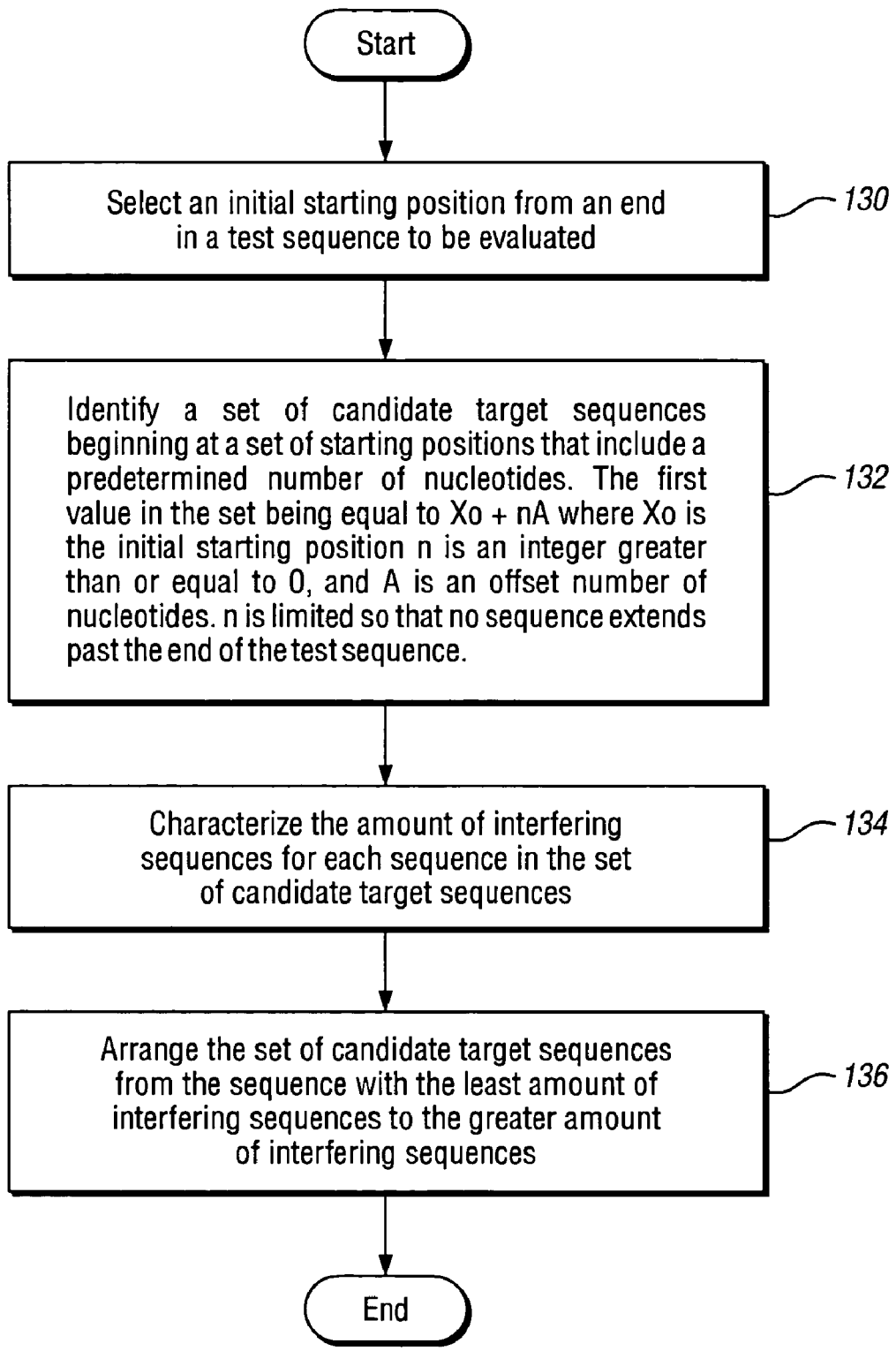
FIG. 3 is a flowchart illustrating the selection of candidate target nucleotide sequences.

In each of the variations of the method exemplified by FIGS. 1 and 2, there is a step in which the candidate target nucleotide sequence is selected. Although any method of selecting candidate target nucleotide sequences may be used and subjected to the algorithm of FIGS. 1 and 2, a systematic approach that may be implemented on a microprocessor based computer is most useful. With reference to FIG. 3 a flowchart of an example of such a systematic approach is provided. The method of this example comprises selecting an initial starting position from an end in the subject nucleotide sequence (Block 130). The end may be either the 3' or the 5' end. Position as used in this context means the number of nucleotides from the end. For example, the 3 position from the 5' end is the third nucleotide from the 5' end. A set of candidate target nucleotide sequences is then identified (Block 132). Each member of the set of candidate target nucleotide sequences begins at a position given by the formula Xo+nA and includes a predetermined number of nucleotides. In this formula, Xo is the initial starting position, n is an integer greater than or equal to 0 and is limited so that no sequence extends past the end of the test sequence, and A is an offset number of nucleotides between adjacent members in the set of candidate sequences. Although any values of Xo and A may be used so long as each is compatible with the length of the subject nucleotide sequence, typically A is from about 1 to about 50 nucleotides while Xo may be a position from the first position to about the 1500th position in the subject nucleotide sequence. Moreover, each member in the set of candidate sequences typically at least 15 nucleotides with about 15 to about 100 nucleotides being useful for many applications. Accordingly, this formula defines a set of starting positions related in a one to one fashion to the position at which each member of the set of target sequences begin. The amount of interfering sequences for each member in the set of candidate target nucleotide sequences is quantified (Block 134). These interfering nucleotide sequences are identified by searching through nucleotide sequences that are likely to be present when utilizing the subject nucleotide sequence. For example, the entire genome of one or more species under investigation may be searched for interfering sequences. Interfering sequences will typically be similar to the candidate target nucleotide sequence. Similar as used herein means that the candidate target nucleotide sequence and each interfering nucleotide sequence have at least a predetermined number of sequential nucleotides in common with the candidate target nucleotide sequence. Typically, the interfering nucleotide sequence will have at least 14 sequential nucleotides in common with the candidate target nucleotide sequences. Alternatively, the interfering nucleotide sequence will have at least 90% of its nucleotides in common with the candidate target nucleotide sequences. A particularly useful approach for quantifying the amount of interfering sequences is by using the BLAST 2 computer program (http://www.ncbi.nlm.nih.gov/blast/b12seq/b12.html) using default parameters. Moreover, the Blast 2 software characterizes the candidate sequences by a Blast index which increases monotonically with the amount of interfering sequences. Finally, the sequences are arranged in order of increasing amount of interfering sequences to form an ordered set of candidate target nucleotide sequences (i.e., from a sequence with the least amount of interfering sequences to a sequence with the greatest amount of interfering sequences) (Block 136.) Moreover, since the Blast 2 software is capable of running in a command line mode, integration into a computer program executing the steps of the methods of the invention is easy.

After the order set of target nucleotide sequences are formed, the algorithms of FIGS. 1 and 2 may be recursively executed with a different candidate target nucleotide sequence selected member from the set of candidate target nucleotide sequences until a predetermined number of target-specific hybridization sequences are identified. Typically, the selected member is sequentially selected from the member of the ordered set with the least amount of interfering sequences to the member with the greatest amount of interfering sequences.

The methods of the invention also include a step in which nucleotides at each of selected positions $P_n$ are replaced with a nucleotide such that the second complementary nucleotide sequence is not complementary to the candidate target nucleotide sequence at each of position $P_n$. An example of implementation of this step on a microprocessor comprises determining a replacement position in the first complementary nucleotide sequence at which a G is located (if present). As set forth below in the experimental section, formation of a mutation in which a single G is replaced can have significant impact on the discrimination of a target-specific hybridization sequence. However, in practice, it is useful to exclude from consideration a predetermined number of nucleotides from each end of the subject nucleotide sequence when making this replacement for G. Next, a set of second complementary nucleotide sequences are created by replacing the G at the replacement position with a nucleotide selected from the group consisting of T/U, C, and A. Each member in the set will only be non-complementary to the candidate target nucleotide sequence as a single position in which a G has been replaced. As used herein, "T/U" means that when the sequence is complementary to a DNA sequence T is used, and when the sequence is complementary to an RNA sequence U is used. However, the set will include every permutation for the replacement of G at all positions at which G occurs in the candidate target nucleotide sequence.

In another variation a mutation may be systematically formed by replacement of C in the candidate target nucleotide sequence. This replacement is particularly useful when the candidate target nucleotide sequence does not contain G so that the first replacement method is unavailable or if the G replacement does not produce a suitable target-specific hybridization sequence. In this replacement method potential replacement positions in the first complementary nucleotide sequence at which a C is located (if present) are determined. Next, a set of second complementary nucleotide sequences are created by replacing the C at the replacement position with a nucleotide selected from the group consisting of T/U, G, and A. Each member in the set will only be non-complementary to the candidate target nucleotide sequence as a single position in which a C has been replaced. However, the set will include every permutation for the replacement of C at all replacement positions at which C occurs in the candidate target nucleotide sequence.

In another variation a mutation may be systematically formed by replacement of A/T in the candidate target nucleotide sequence. This replacement is particularly useful when the candidate target nucleotide sequence does not contain G or C so that the first replacement method is unavailable or if the G or C replacement does not produce a suitable target-specific hybridization sequence. In this replacement method potential replacement positions in the first complementary nucleotide sequence at which a A or a T/U is located are determined. Next, a set of second complementary nucleotide sequences are created by replacing the A at the replacement positions with a nucleotide selected from the group consisting of T/U and C or by replacing T/U at the replacement positions with a nucleotide selected from the group consisting of A and C. Each member in the set will only be non-complementary to the candidate target nucleotide sequence as a single position in which a A or T/U has been replaced. However, the set will include every permutation for the replacement of A or T/U at all replacement positions at which A or T/U occurs in the candidate target nucleotide sequence.

In yet another variation of the present invention, incorporation of mutations at two positions of the second complementary nucleotide sequences is found to provide superior discrimination in some situations. The step of replacing nucleotides at each of selected positions $P_n$ is accomplished in this variation by determining replacement positions in the first complementary nucleotide sequence at which a G×G fragment is located, wherein a predetermined number of nucleotides from each end of the subject nucleotide sequence are excluded from consideration when determining the replacement position and X is any nucleotide. Finally, the second complementary nucleotide sequences are created by replacing each G in the G×G fragment independently with a nucleotide selected from the group consisting of A, T/U, and C.

In still another variation of the present invention, incorporation of mutations at two positions of the second complementary nucleotide sequences is found to provide superior discrimination in some situations. The step of replacing nucleotides at each of selected positions $P_n$ is accomplished in this variation by determining replacement positions in the first complementary nucleotide sequence at which a GG fragment is located, wherein a predetermined number of nucleotides from each end of the subject nucleotide sequence are excluded from consideration when determining the replacement position. Finally, the second complementary nucleotide sequences are created by independently replacing each G in the GG fragment with a nucleotide selected from the group consisting of A, T/U, and C.

In still another variation of the present invention, incorporation of mutations at two positions of the second complementary nucleotide sequences is found to provide superior discrimination in some situations. The step of replacing nucleotides at each of selected positions $P_n$ is accomplished in this variation by determining replacement positions in the first complementary nucleotide sequence at which a CG (or GC) fragment is located, wherein a predetermined number of nucleotides from each end of the subject nucleotide sequence are excluded from consideration when determining the replacement position. Finally, the second complementary nucleotide sequences are created by independently replacing C in the CG (or GC) fragment with a nucleotide selected from the group consisting of A, T/U, and G and replacing G in the CG (or GC) fragment with a nucleotide selected from the group consisting of A, T/U, and C.

In yet another variation of the present invention, incorporation of mutations at two positions of the second complementary nucleotide sequences is found to provide superior discrimination in some situations. The step of replacing nucleotides at each of selected positions $P_n$ is accomplished in this variation by determining replacement positions in the first complementary nucleotide sequence at which a CC fragment is located, wherein a predetermined number of nucleotides from each end of the subject nucleotide sequence are excluded from consideration when determining the replacement position. Finally, the second complementary nucleotide sequences are created by independently replacing each C in the CC fragment with a nucleotide selected from the group consisting of A, T/U, and G.

Figure 4:
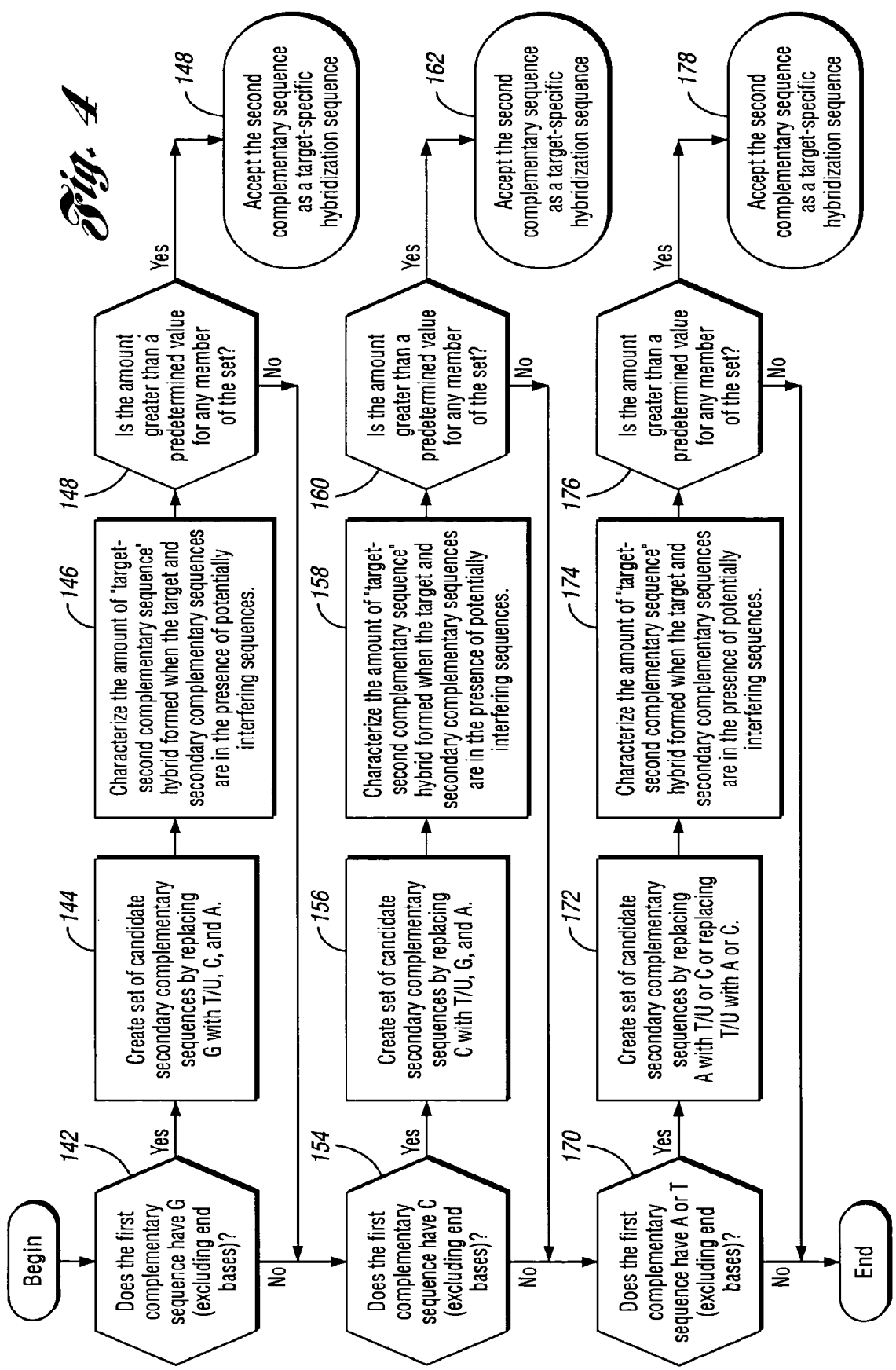
FIG. 4 is a flowchart illustrating the incorporation of single mutations into the second complementary nucleotide sequences.
Figure 5B:
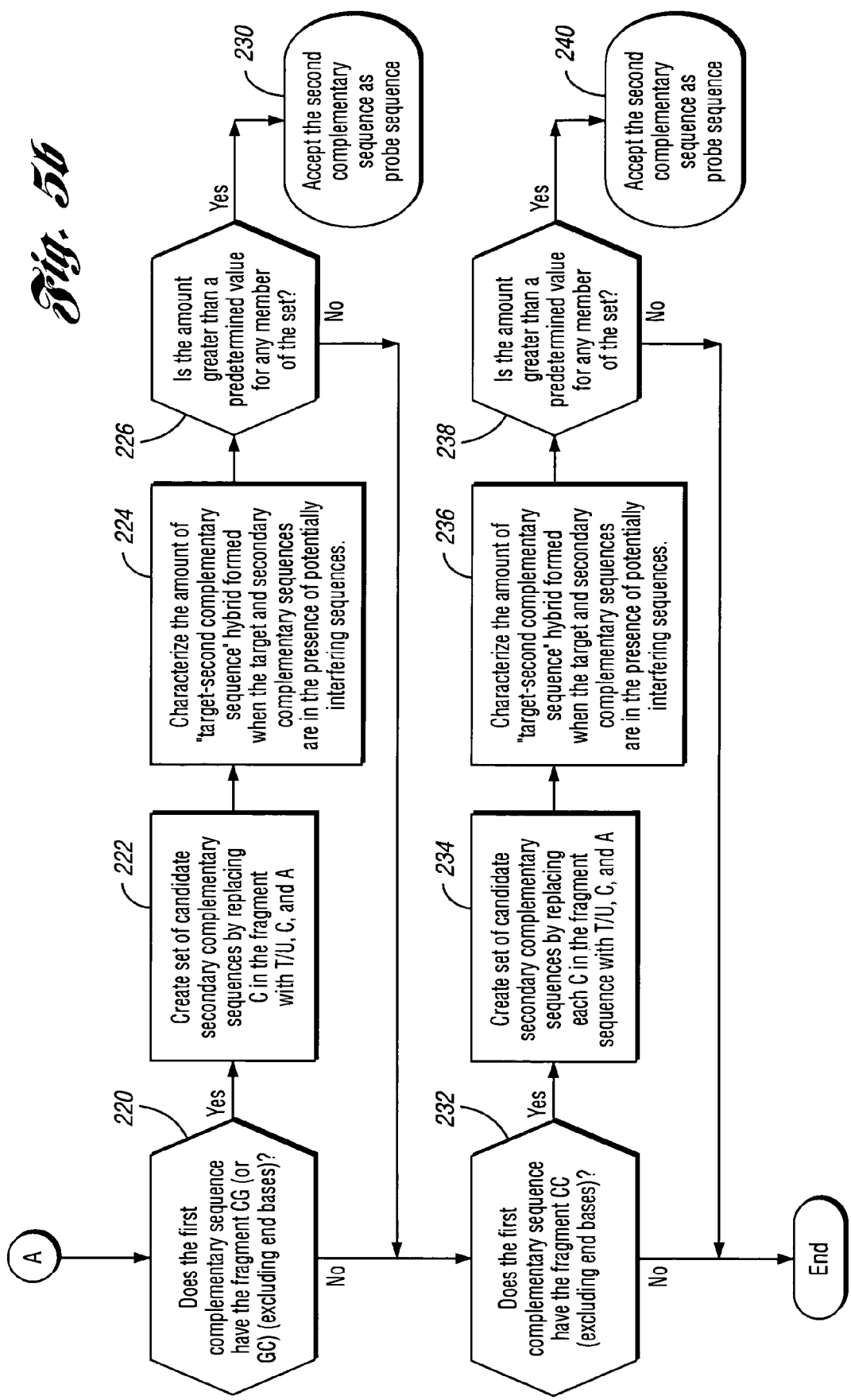
FIG. 5 is a flowchart illustrating the incorporation of double mutations into the second complementary nucleotide sequences.

In another variation of the present invention, a method of designing a target-specific hybridization sequence is provided. The method of this embodiment incorporates into a computer implemented algorithm, the criteria for forming single mutations and double mutations as set forth above. FIG. 4 provides an integrated method for forming single mutations while FIG. 5 provides an integrated method for forming double mutations. Each of these algorithms are executed as part of the general schema for designing target specific hybridization sequences illustrated in the flowchart of FIG. 6. With reference to FIGS. 4 and 6, the method of this embodiment comprises selecting a candidate target nucleotide sequence in a subject nucleotide sequence in the same manner as set forth above for FIGS. 1 and 2 (block 100.) Again, the characteristics of the subject nucleotide sequence are the same as set forth above. A first complementary nucleotide sequence to the target nucleotide sequence is identified (Block 102). Next, a second complementary nucleotide sequence having a mutation is constructed (Block 140) in accordance with the algorithm of FIG. 4. As set forth in decision block 142, the algorithm determines if the first complementary nucleotide sequence has any G. Usually, this is done while excluding from consideration a predetermined number (typically about 3) of nucleotides from each end of the first complementary nucleotide sequence. A set of replacement positions $P_n$ in the first complementary nucleotide sequence are created by locating each position at which a G is located. A set of second complementary nucleotide sequences is created by replacing each G at the replacement positions $P_n$ with a nucleotide selected from the group consisting of T/U, C, and A (block 144.) Since only single mutations are being considered at this point, each member of the set of second complementary nucleotide sequences has a single G replaced. The amount of the "target-second complementary nucleotide sequence" hybrid is formed when the target and second complementary nucleotide sequences are characterized in the same manner as set forth above (block 146). In decision block 148, a determination is made as to whether the amount of the "target-second complementary nucleotide sequence" hybrid is greater than a predetermined value. The specifics of this determination are the same as that set forth above. Each member in the set of second complementary nucleotide sequences for which the amount of the "target-second complementary nucleotide sequence" hybrid is greater than the predetermined value is accepted as a target-specific hybridization sequence (block 150).

Still referring to FIGS. 4 and 6, if none of the set of second complementary nucleotide sequences are greater than the predetermined value or if the candidate target nucleotide sequence did not contain G (or if additional potential target-specific hybridization sequences are desired), a determination is made as to whether the candidate target nucleotide sequence has C (decision block 154). In a similar fashion, a set of replacement positions $P_n$ in the first complementary nucleotide sequence are identified by locating each position in the candidate target nucleotide sequence at which a C is located. The set of second complementary nucleotide sequences is created by replacing each C at the replacement positions $P_n$ with a nucleotide selected from the group consisting of T/U, G, and A (block 156.) Since only single mutations are being considered at this point, each member of the set of second complementary nucleotide sequences has a single C replaced. The amount of the "target-second complementary nucleotide sequence" hybrid is formed when the target and second complementary nucleotide sequences are characterized in the same manner as set forth above (block 158). In decision block 160, a determination is made as to whether the amount of the "target-second complementary nucleotide sequence" hybrid is greater than a predetermined value. The specifics of this determination are the same as that set forth above. Each member in the set of second complementary nucleotide sequences for which the amount of the "target-second complementary nucleotide sequence" hybrid is greater than the predetermined value is accepted as a target-specific hybridization sequence (block 162).

Still referring to FIGS. 4 and 6, if none of the set of second complementary nucleotide sequences are greater than the predetermined value or if the candidate target nucleotide sequence did not contain G or C (or if additional potential target-specific hybridization sequences are desired), a simultaneous determination is made as to whether the candidate target nucleotide sequence has A or T/U (decision block 170). A set of replacement positions $P_n$ in the first complementary nucleotide sequence are identified by locating each position in the candidate target nucleotide sequence at which an A and T/U is located. The set of second complementary nucleotide sequences is created by replacing each A at the replacement positions $P_n$ corresponding to an A with a nucleotide selected from the group consisting of C and T/U and by replacing each T/U at the replacement positions $P_n$ corresponding to a T/U with a nucleotide selected from the group consisting of A and C (block 172). Since only single mutations are being considered at this point, each member of the set of second complementary nucleotide sequences has either a single A replaced or a single T/U replaced. The amount of the "target-second complementary nucleotide sequence" hybrid is formed when the target and second complementary nucleotide sequences are characterized in the same manner as set forth above. (block 174). In decision block 176, a determination is made as to whether the amount of the "target-second complementary nucleotide sequence" hybrid is greater than a predetermined value. The specifics of this determinagion are the same as that set forth above. Each member in the set of second complementary nucleotide sequences for which the amount of the "target-second complementary nucleotide sequence" hybrid is greater than the predetermined value is accepted as a target-specific hybridization sequence (block 178).

With reference to FIGS. 5 and 6, a method utilizing double mutations is provided. The method of this variation comprises selecting a candidate target nucleotide sequence in a subject nucleotide sequence in the same manner as set forth above for FIGS. 1 and 2 (block 100.) A first complementary nucleotide sequence to the target nucleotide sequence is identified (Block 102). Again, the characteristics of the subject nucleotide sequence are the same as set forth above. Next, a second complementary nucleotide sequence having a mutation is constructed (Block 140) in accordance with the algorithm of FIG. 5. As set forth in decision block 200, the algorithm determines if the first complementary nucleotide sequence has any G×G fragments (X is any nucleotide). Usually, this is done while excluding from consideration a predetermined number (typically about 3) of nucleotides from each end of the first complementary nucleotide sequence. A set of replacement positions $P_n$ in the first complementary nucleotide sequence are created by locating the position for each G×G fragment. A set of second complementary nucleotide sequences is created by independently replacing each G in a G×G fragment with a nucleotide selected from the group consisting of T/U,C, and A (block 202). Since only double mutations are being considered at this point, each member of the set of second complementary nucleotide sequences only have a single G×G fragment undoing the double replacement. The amount of the "target-second complementary nucleotide sequence" hybrid formed when the target and second complementary nucleotide sequences is characterized in the same manner as set forth above (block 204). In decision block 206, a determination is made as to whether the amount of the "target-second complementary nucleotide sequence" hybrid is greater than a predetermined value. The specifics of this determination are the same as that set forth above. Each member in the set of second complementary nucleotide sequences for which the amount of the "target-second complementary nucleotide sequence" hybrid is greater than the predetermined value is accepted as a target-specific hybridization sequence (block 208).

Still referring to FIGS. 5 and 6, if none of the set of second complementary nucleotide sequences are greater than the predetermined value or if the candidate target nucleotide sequence did not contain a G×G fragment (or if additional potential target-specific hybridization sequences are desired), the algorithm determines if the first complementary nucleotide sequence has any GG fragments (Block 210). Usually, this is done while excluding from consideration a predetermined number (typically about 3) of nucleotides from each end of the first complementary nucleotide sequence. A set of replacement positions $P_n$ in the first complementary nucleotide sequence are created by locating the position for each GG fragment. A set of second complementary nucleotide sequences is created by independently replacing each G in a GG fragment with a nucleotide selected from the group consisting of T/U,C, and A (block 212.) Since only double mutations are being considered at this point, each member of the set of second complementary nucleotide sequences only have a single GG fragment undgoing the double replacement. The amount of the "target-second complementary nucleotide sequence" hybrid formed when the target and second complementary nucleotide sequences is characterized in the same manner as set forth above (block 214). In decision block 216, a determination is made as to whether the amount of the "target-second complementary nucleotide sequence" hybrid is greater than a predetermined value. The specifics of this determination are the same as that set forth above. Each member in the set of second complementary nucleotide sequences for which the amount of the "target-second complementary nucleotide sequence" hybrid is greater than the predetermined value is accepted as a target-specific hybridization sequence (block 218). In Blocks 220-240, the method for replacing CG and CC fragments are illustrated and are completely analogous.

In another embodiment of the present invention, a computer readable medium having instructions thereon that perform the methods set forth above and illustrated in FIGS. 1-6 is provided. This computer readable medium may be any medium capable of storing such instructions. Examples include, RAM memory, ROM memory, hard drives, magnetic tapes, floppy drives, CDROM, CRRAM, CDR, DVD, DVDR, and the like.

In another embodiment of the present invention, a (actual) target-specific hybridization sequence is provided. The target-specific hybridization sequence is demonstrated as having improved discrimination performance by the methods set forth above. The target-specific hybridization sequence of the invention includes a sequence of nucleotides that are complementary to a target nucleotide sequence except for the occurrence of one or more mutations at selected positions $P_n$. These mutations are created by replacing one or more nucleotides in a perfectly-matched complementary nucleotide sequence by a natural nucleotide that renders the sequence of nucleotides non-complementary at positions $P_n$. The perfectly-matched complementary sequence is perfectly complementary to the target nucleotide sequence. The feasibility and the most effective mutations for achieving improved discrimination are set forth above for the methods of the invention. In some variations the $P_n$ are not within a predetermined number of nucleotides from an end of the sequence. In some variations of this embodiment, the target-specific hybridization sequence includes the single and double mutations set forth above for the methods of the invention. Specifically, the replacements for G, C, A, and T/U as well as the double replacements for GxG, GG, CG, and CC fragments as set forth above are incorporated into the target-specific hybridatization sequence of the invention. Moreover, when the second complementary nucleotide sequence has more than 2 mutations, the mutations may be the the sum of the single and double mutation algorithms. For example, a three mutation sequence is formed by combining a single and double mutation or three single mutations. In some variations, the target-specific hybridatization sequence is a dsRNA sequence having a sense and anti-sense strand wherein either the sense or anti-sense strand is the target-specific hybridization sequence.

The following examples illustrate the various embodiments of the present invention. Those skilled in the art will recognize many variations that are within the spirit of the present invention and scope of the claims.

Figure 8A:
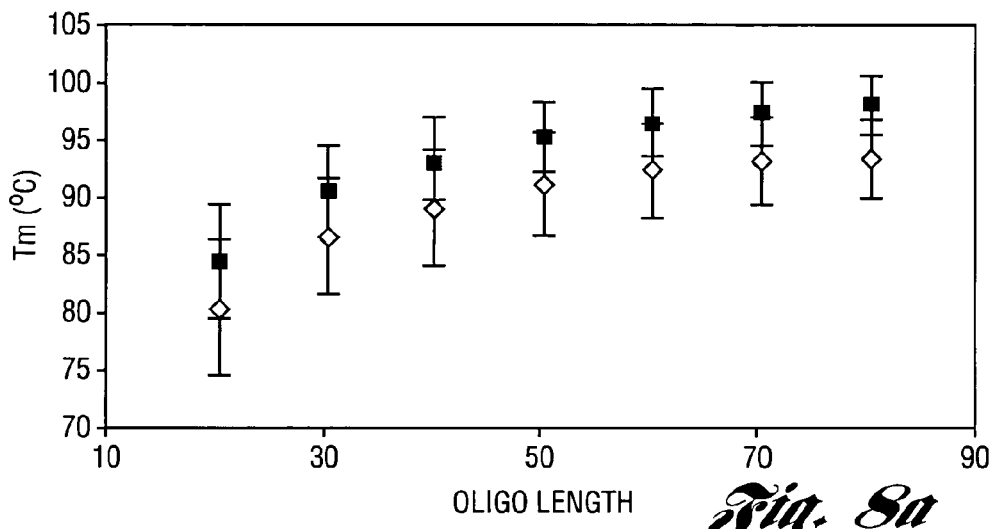
FIG. 8 provides plots of the hybridization $T_m$ dependency (A) and $T_m$ variance ($\Delta T_m$) dependency (B) on oligonucleotide length due to single-point mutation based on OMP calculation. Open diamonds represent data obtained from oligo sequences of EphB1 mRNA. Filled squares represent data obtained from IgG Fc binding protein mRNA. Shorter oligos are subsets of longer ones. Dotted lines in B are fitted graphs providing the exponent a in equation 5 in the main text. One original oligo pair in (A) produces (3×oligo length) mutated pairs in (B)

The $\Delta T_m$ determined by single-point mutation and double-point mutations calculations as well as the calculated sample probes set forth below verify utility of the steps assembled to form the methods of the present invention. In these simulations, oligos of various lengths (20, 30, 40, 50, 60, 70 and 80mer: shorter oligos are subsets of longer ones) were selected from human mRNA sequences: EphB1 mRNA (EPHB1, gi: 4758283) and IgG Fc binding protein mRNA (FCγBP, gi: 4503680). Marks are set at every 100th position from the 3'-end and copied 20 sequences from the marks to the 5'-end to obtain 20mer oligonucleotides providing a varied sub-sample of all possible oligos. Since longer oligonucleotides were prepared in a similar way, all the shorter ones were subsets of the longer ones. Point-mutated oligos (single or double) were systematically selected from these original oligo sequences. The hybridization $T_m$ of original and mutated oligos with the complementary target sequence was calculated. The OMP parameters used for the calculations were oligonucleotide concentration 1 mM, Na⁺ concentration 0.5 M, and assay temperature 37° C. Each original sequence mutated to three other sequences. After the hybridization $T_m$ was calculated, $T_m$ differences between the original pair and the mutated ones were calculated and the histograms of $\Delta T_m$ obtained for categories such as position, sequence change, distance between mutation sites and GC content. Each histogram step is 1° C. and mean and standard deviation were calculated from the histogram values. Exponents shown in FIGS. 8 and 10 were obtained using power fitting in Microsoft Excel.

In the probe selection program, an oligo probe and a corresponding sequence of genes is used for OMP calculation to reduce computation time. When the OMP input contains nucleotides A and B, the OMP output reports each calculated concentration and $T_m$ of ensembles such as folded A, A-A dimer, folded B, B-B dimer, A-B dimer and random coils. Hybridization percentage is defined as the percentage of A-B dimer among the ensembles at the assay temperature. Parameters for probe design were probe length=60mer, assay temperature=80° C., Na⁺ concentration=0.5 M, target and probe concentrations=1 mM, probe folding $T_m$<60° C., hybridization percentage of probe and target gene >95%, and hybridization percentage of probe and non-target gene <20%.

Results $\Delta T_m$ by Single-Point Mutation

Two human mRNA sequences were used as templates for oligo generation. The sequences, EphB1 mRNA (EPHB1, gi: 4758283) and IgG Fc binding protein mRNA (FCγBP, gi: 4503680), have no significant similarity as assessed by the BLAST 2 program (http://www.ncbi.nlm.nih.gov/blast/b12seq/b12.html) using default parameters. Their properties, obtained from the PROLIGO oligo parameter calculation website (http://proligo2.proligo.com/Calculation/calculation.html), and $T_m$ calculated from the following equation are shown in Table 1:

$$T_m = 81.5 + 16.6 \cdot \log_{10}\{[Na^+]/(1+0.7[Na^+])\} + 0.41(\% \, G+C) - 500/D - P \qquad 3$$

where D is duplex length and P is percent mismatch, and [Na⁺]=0.5 M. These target genes were selected to demonstrate that our oligo probe design approach is independent of the sequence content of target genes. Oligo probes of various lengths were selected from each target gene as described in Materials and Methods.

TABLE 1

General properties of EPHB1 and FC⊃BP

| Gene | Accession | Length | GC content (%) | MW (g/mol) | Tm (° C.) |
|---|---|---|---|---|---|
| EPHB1 | NM_004441.1 | 3871 | 54 | 1194541 | 98.0 |
| FC⊃BP | NM_003890.1 | 16382 | 63 | 5057549 | 102.0 |

Figure 7A:
FIG. 7 provides schematic diagrams of oligonucleotides. (A) Original Tm is defined as the hybridization Tm of the perfect match pair. The point-mutated site is described in X and the mutated $T_m$ is defined as their hybridization Tm. Three possible mutations occur at each site. (B) The mutation site is defined as the position from the end of the oligos, ignoring 3' and 5' direction. A single-point mutation is performed at position 5. (C) In the two-point mutations, the reference position is defined as a smaller position number between two mutation sites. The distance is defined as 1 plus the number of nucleotides between them.

The hybridization $T_m$ for oligos of various lengths and their complementary target sequences was computed and defined as the original $T_m$ ($T_m$ original) (FIG. 7A). The $T_m$ calculations were performed as detailed above. The average hybridization $T_m$ for each oligo length based OMP calculation is roughly 4-5° C. higher with FCγBP than that with EPHB1 (FIG. 8A), consistent with the $T_m$ differences between the two entire genes based on % GC calculation, whose values are presented in Table 1. Note that overall temperatures are roughly 10° C. higher than calculated conditions at [Na⁺]=

100 mM and at the same oligo concentration of 1 mM. $T_m$ values generally depend on GC content and secondary structures. The standard deviation of oligo hybridization $T_m$ from FCγBP is smaller than that from EPHB1 in calculation, possibly because the number of oligos obtained from FCγBP is much greater due to the longer sequence. The mutated $T_m$ ($T_m$ mutated) was defined as the hybridization $T_m$ between a point-mutated strand and the reverse complementary sequences of the original target strand (FIG. 7A). The $T_m$ variance by a mutated sequence, $\Delta T_m$ is as follows:

$$\Delta T_m = T_{m\ mutated} - T_{m\ original} \qquad 4$$

Figure 8B:
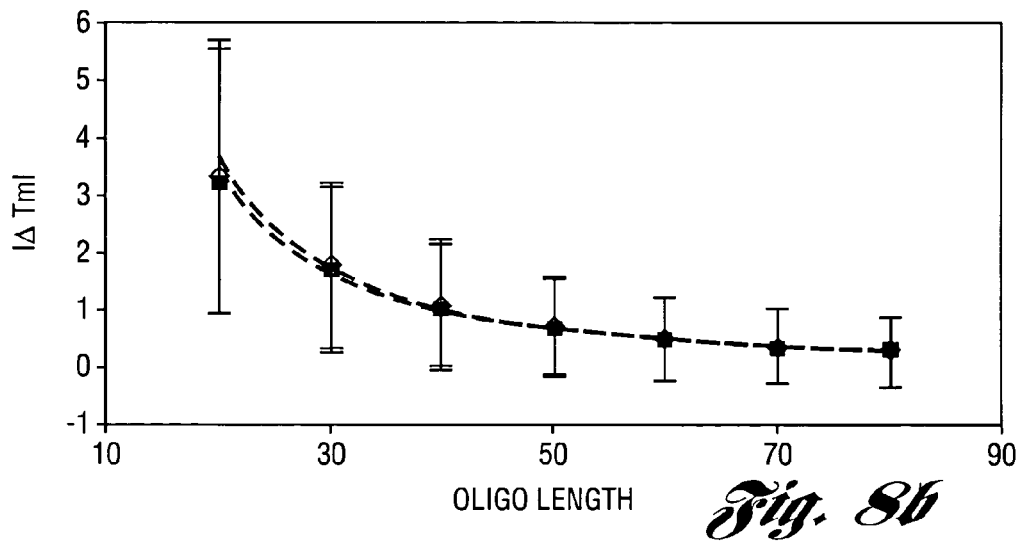

Interestingly, calculated $\Delta T_m$ for the mutated oligo probes in both genes has the same dependency on oligo length with virtually the same standard deviation as indicated by the error bars (FIG. 8B). The dependency can be described as $$|\Delta T_m| \propto L^\alpha \qquad 5$$

where $|\Delta T_m|$ is the absolute value of the mean $\Delta T_m$ and L is the oligo length. Both exponents α of EPHB1 and FC⊇BP oligos are −1.87. All standard deviations in FIG. 8 diminish as the oligo length increases. Interestingly, the calculated $\Delta T_m$ of the two mRNAs showed the same α and standard deviation despite the content differences in the two genes.

Figure 7B:
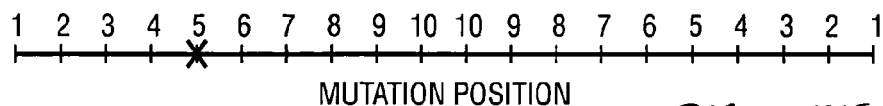
Figure 9A:
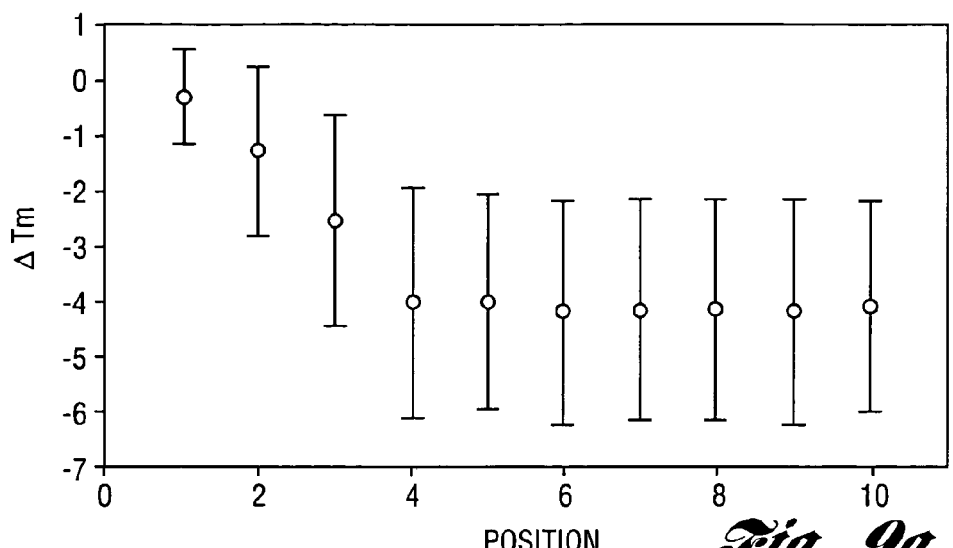
FIG. 9 provides plots of the calculated $\Delta T_m$ dependency on nucleotide mutation and position in 20mer oligonucleotides. (A) Average $\Delta T_m$ values of all sequence changes at each position are shown with standard deviations. (B) Average $\Delta T_m$ values of each sequence change are shown. Data point patterns represent the original sequences: filled shape, A; grey colored, T; open, C; and lined, G, while shapes represent the mutated sequences: square, A; diamond, T; circle, C; and triangle, G (filled diamonds, from A to T; filled circles, A to C; filled triangles, A to G; grey squares, T to A; grey circles, T to C; grey triangles, T to G; open squares, C to A; open diamonds, C to T; open triangles, C to G; lined squares, G to A; lined diamonds, G to T; and lined circles, G to C). (C) $\Delta T_m$ dependency on nucleotide in 20mer oligonucleotides excluding the three end points. (D) All $\Delta Td$ values of each sequence change Urakawa et al. are shown at each position from 5'-end excluding the three end positions. Pattern and shape representations are as in (B). A datapoint indicated with an arrow is a [G,C] mismatch case, which will be ignored in the comparison.
Figure 9B:
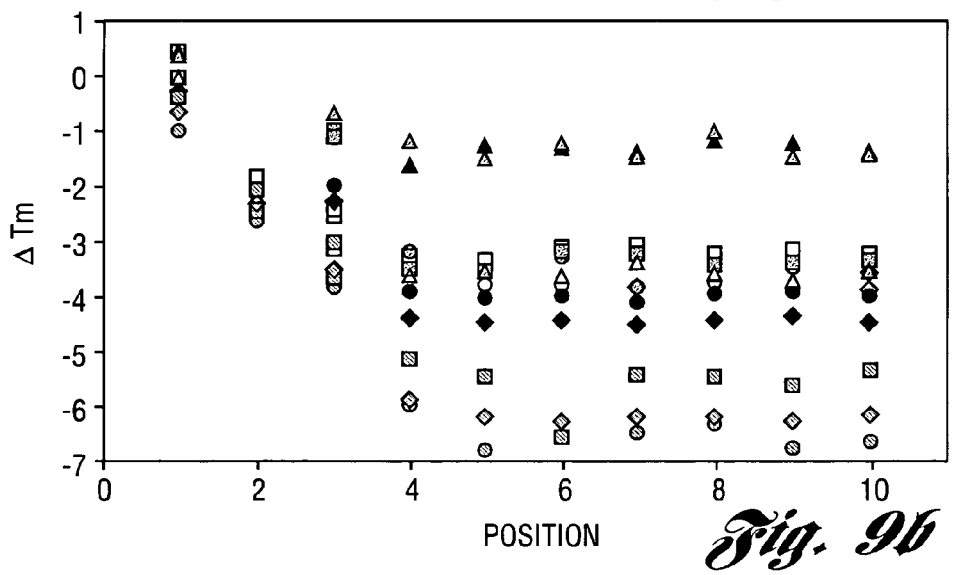
Figure 9C:
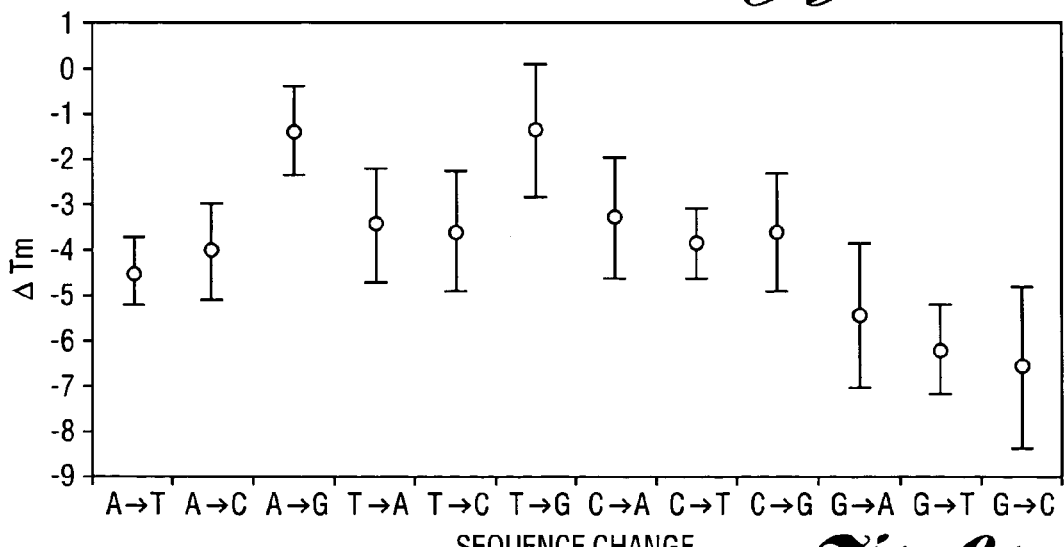
Figure 9B:
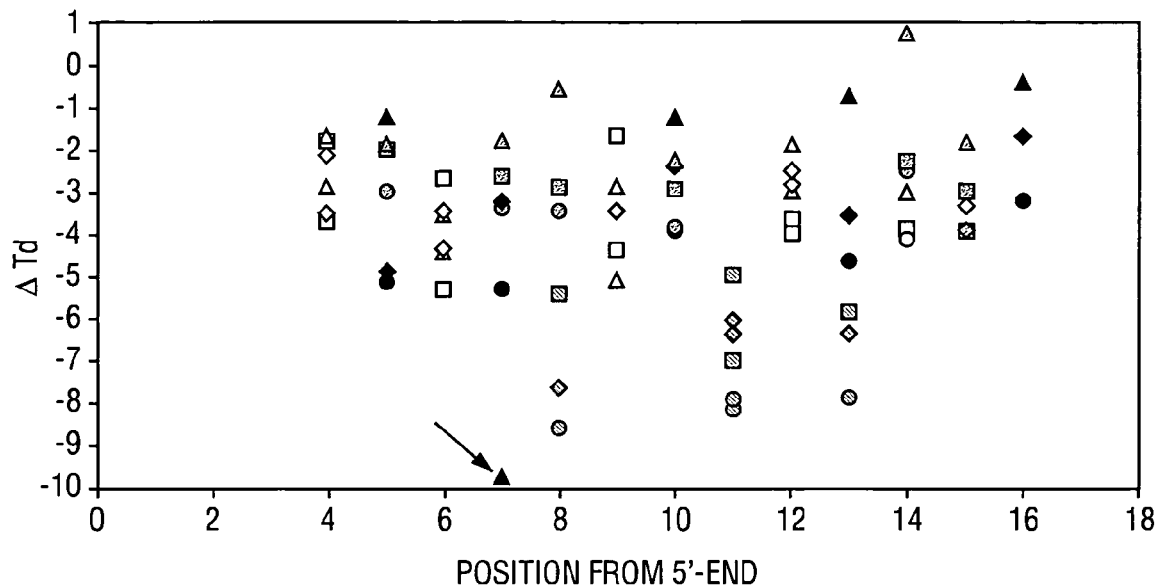

Calculated $\Delta T_m$ of each mutation site for each oligo probe were investigated to assess the nature of the large standard deviation shown in FIG. 8 and to provide guidelines for oligo probe design. The mutation site is defined as the position from the end of the oligo, ignoring 5' and 3' direction. Position 1 refers to the two end positions of each oligo, position 2 the next positions toward the center, and so forth (FIG. 7B). Mutation site dependency of oligo length 20 is shown in FIG. 9A. A slight change in calculated $T_m$ with relatively small standard deviation is observed at position 1, and $|\Delta T_m|$ increases with larger standard deviation as the position number increases up to four. There is no mutation site dependency from position 4 towards the center. This trend is independent of the specific nucleotide mutation (FIG. 9B, standard deviations not shown for data clarity). When the mutation site is at position 2, two groups appear: practically no change in $T_m$ (mutations from either A or T), and the beginning of significant $T_m$ change (mutations from either C or G). Many mutations present changes in $T_m$ and distinctively larger standard deviations at position 3, while mutations from T undergo little $T_m$ change. However, no mutation shows position dependency except the three end positions. $\Delta T_m$ dependency on nucleotide mutation of oligo 20mer, excluding the last three end positions, is shown in FIG. 9C. When A or T are mutated to G, $|\Delta T_m|$ is the lowest. $|\Delta T_m|$ by mutation from G is larger than in any other cases. Although the mutation from G to C yields the greatest change in calculated $T_m$, the standard deviation is much larger than the mutation from G to T, which presents a similar $T_m$ change (clearer for oligo length 30 and longer). All these features hold true for other oligo lengths as well. The experimental data from Urakawa et al. excluding the last three end positions are shown in FIG. 9D for comparison. (Urakawa et al *Optimization of single-base pair mismatch discrimination in oligonucleotide microarrays*. Appl. Environ. Microbiol., 69, 2848-2856 (2003).) The shading and shape are coded as in FIG. 9B. Since the lengths of oligo1 and oligo2 are different, the data is displayed at each position from the 5'-end instead of position definition in FIG. 7B. For the most part, the data falls within the range of the FIG. 9B trend. Filled and gray triangles (mutation from A and T to G) present the least $T_m$ changes; lined shapes (mutations from G) represent most $T_m$ changes. $\Delta T_d$ differences among positions of the same shading and shape are around 2° C., while differences among specific sequences at certain positions (8 and 13 positions from 5'-end) can exceed 6° C.

$\Delta T_m$ by Two-Point Mutation

Figure 10:
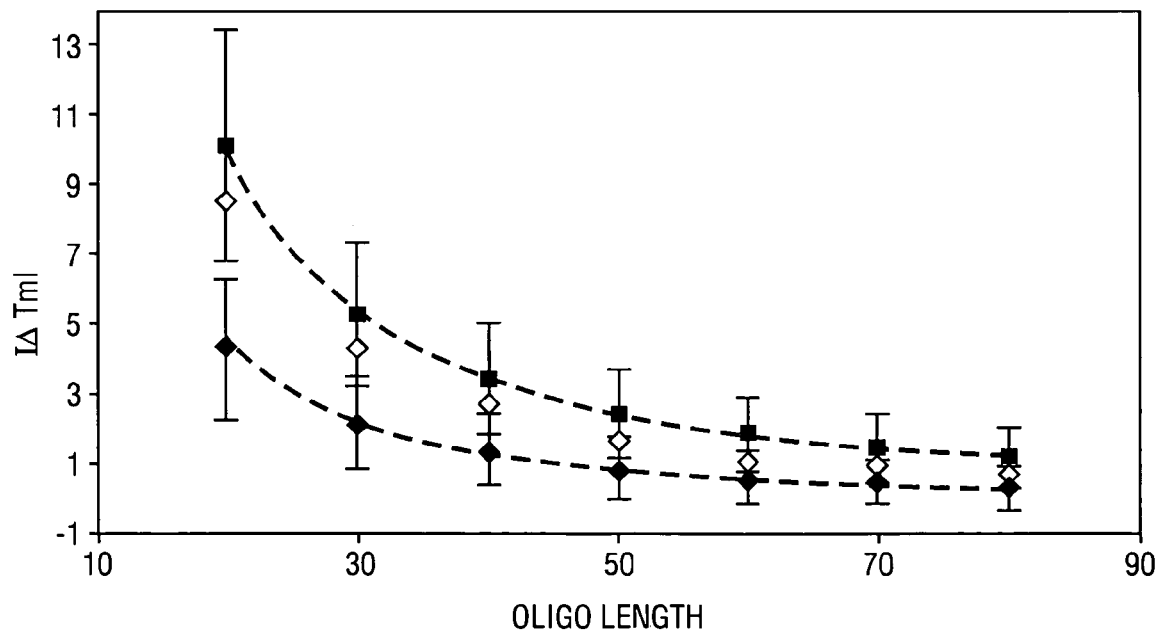
FIG. 10 provides plots of the calculated $\Delta T_m$ dependency on oligonucleotide length by single and two-point mutations excluding the three end points. Filled diamonds represent single-point mutations, filled squares two-point mutations, and open diamonds represent 2×$\Delta T_m$ by single-point mutations. Dotted lines are fitted graphs.

Single-point mutations were compared with two-point mutations of oligos from EPHB1 mRNA. FIG. 10 presents calculated $\Delta T_m$ as a function of oligo length excluding mutations of the last three end positions. To simplify the variables, only 20 positions from the 3'-end of oligonucleotides are included in the two-point mutation data. The values of $2 \times \Delta T_m$ by single-point mutation are also presented to show that calculated $\Delta T_m$ by two-point mutation is not simply additive of $\Delta T_m$ by single-point mutation calculation, indicating synergetic effects in two-point mutation. The exponent a in equation 5 of the single-point mutation without the last three end positions is slightly reduced at −1.93 from FIG. 8B. The exponent in the two-point mutation is −1.55, showing a more sensitive dependency on length.

Figure 7C:
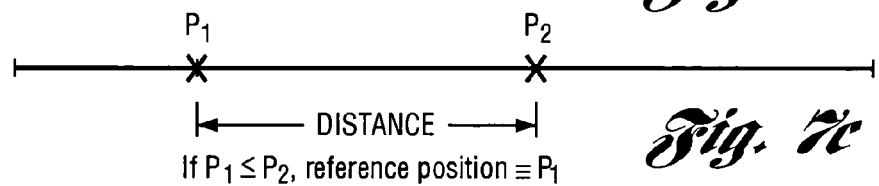

The reference position is defined as the smaller position of the two mutation sites in a two-point mutation. The distance is defined as one plus the number of nucleotides between them (FIG. 7C). The $\Delta T_m$ dependency of oligo 20mer on the reference position and distance is presented in FIG. 11. By definition, increasing distance refers to the second mutation site moving towards the other oligo-chain end until the second site reaches the same position number as the reference position. Open shapes represent $\Delta T_m$ values of mismatch pairs when at least one of the mutation sites is at the last three end positions; filled shapes indicate both mutation sites are at inner positions. The greatest $|\Delta T_m|$, along with the smallest standard deviation, is observed when two consecutive sites (distance of one) are mutated at position six or greater. For a fixed distance between two mutation sites, there is no position dependency except with the last three positions (reference position≦3) and at reference-distance pairs 4-1 and 4-2. Also, for fixed reference positions, very little distance dependency is observed except when the pairs are nearest neighbors or when both mutation sites are among the last four end positions. Note that the last fourth end positions do not show differences from the inner ones when each mutation occurs at each other's chain side (1-16, 2-15, 3-14). On the other hand, when both mutations occur on the same side of chain, mutations at 3-2, 3-3 and 4-2 show distance dependency. These features also hold true for longer oligo lengths. Mutations at 4-3, 5-1 and 5-2 show moderate reference position or distance dependencies, which disappear at oligo lengths longer than 30.

Figure 12:
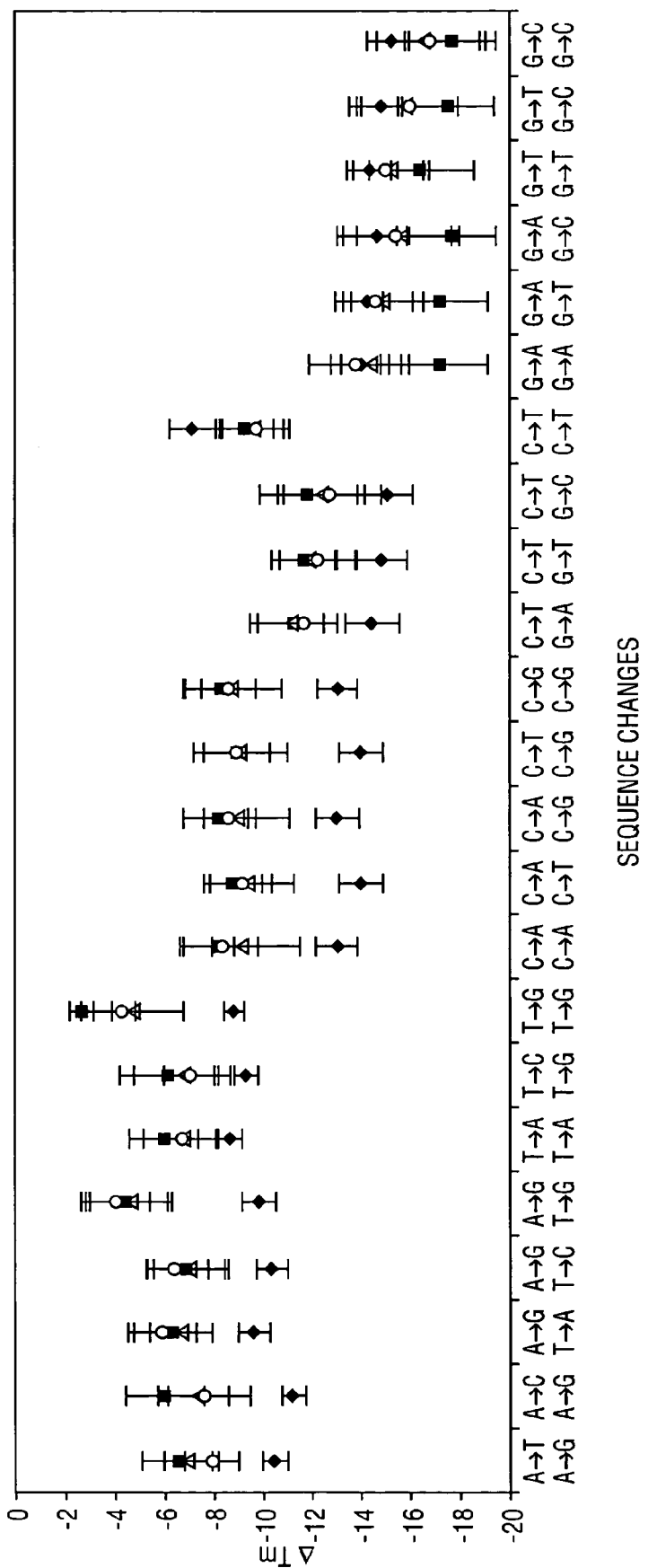
FIG. 12 provides a summary of specific sequence changes correlated with significantly different calculated $\Delta T_m$ of 20mer oligonucleotides in the distance between mutation sites at fixed position 10. The distances from position 10 are one (filled diamond), two (filled square), three (open triangle) and four (open circle).

With two-point mutations, the $\Delta T_m$ dependency on the specific nucleotide mutation is similar to that observed with single-point mutations. When both mutations are from G, $|\Delta T_m|$ is the largest, whereas when both mutations are from A or T to G, $|\Delta T_m|$ is the least. Some distinctive features related to the distance between mutation sites are observed in the double mutations. FIG. 12 shows specific sequence changes correlated with differences in distance between mutation sites in 20mer oligos. The distance is varied between mutation sites from one to four while fixing one mutation site position at ten. Nucleotide-specific mutations that provided a significantly larger $|\Delta T_m|$ in the nearest neighbor position as compared to distances greater than one are shown to the left of the {C to T, C to T} double mutation in FIG. 12. The double mutations showing a relatively larger $|\Delta T_m|$ in the next nearest neighbor mutation cases as compared to the other positions are shown on the right side of the figure. There are three mutation categories where two consecutive mismatches (filled diamonds in the figure) provide significantly larger $|\Delta T_m|$: (i) both mutations are from A or T and at least one of them goes to G, except for {A to G, A to G} mutations; (ii) both mutations are from C, except {C to T, C to T} mutations; and (iii) one mutation is from C to T and the other is from G. Note that mutations from both A to G and C to T, which are exceptional cases of the above categories, lead to [G, T] mismatches. On the other hand, when both the mutations are from G, mismatches at the next nearest neighbor positions (filled rectangular) provide relatively larger $|\Delta T_m|$ than any other mutation distances.

Point-Mutated Probe Sample

A software program based on the thermodynamic calculation and sequence similarity test was developed to design oligo probes that hybridize with only one specific gene among the entire genome. However, using oligo probes perfectly matched to the target gene made it difficult to select probes for genes in large families with significant similarity, such as the P450s. To avoid cross-hybridization in a microarray experiment, it is desirable to have a probe hybridize with its complementary target at a $T_m$ that is significantly higher than the $T_m$ of the same probe matched with any other gene product in the transcriptome. It is also desirable to have all probes in one microarray hybridize with their targets at similar $T_m$ values. Based on the above results, point mutations were selected to design probes that distinguish similar genes. One example is P450 CYP21A2 human mRNA (gi: 20522237, accession:NM_000500.4). The test database was downloaded from the NCBI RefSeq human mRNA site (ftp://ftp.ncbi.nih.gov/refseq/H_sapiens/mRNA_prot). CYP21 A2 has high similarity with P450 pseudogene (CYP21A1P) on chromosome 6 (gi: 20270487, accession: NG_001111.1) among the test database. A BLAST search (with word size 8) reported most sequences in CYP21A2 have 97-100% identity with CYP21A1P. One lowest similarity report was 92% identity among 155 sequences. The only non-reported part was positions between 828 and 854 from the 5'-end, which are only 26 sequences surrounded by 98% identity sequences. Moreover, these 26mer reported sequence similarities with other genes in the test database. Our probes were 60mer, with one of the selection criteria being over 95% hybridization at assay temperature (80° C.). Varying the probe size from 60mer should not improve the selection much.

One probe perfectly matching a target sequence has cross hybridization potential with CYP21A1P and more than 10 other genes, among them RAP1, GTPase activating protein 1 (RAP1GA1) mRNA (gi: 20270487, accession: NG_001111.1) and human double homeobox, 2 (DUX2) mRNA (gi:21687002, accession: NM_012147.2), based on a BLAST search of the test database and $T_m$ calculations. Using three-point mutation, the probe was redesigned to avoid cross-hybridization. Calculated hybridization $T_m$ and hybridization percentage at 80° C. of both the probes and target/non-target genes are in Table 2. Bold letters are the mutation sites; lower case letters represent mutation sequences. At assay temperature 80° C., both perfect match and three-point mismatch probes will hybridize 100% with the target gene if there are no other competing genes. However, calculated hybridization $T_m$ values of a perfect match probe with CYP21A1P, RAP1GA1 and DUX2 are around 80° C., leaving open the possibility of cross-hybridization. Meanwhile, the mismatch probe lowered the calculated hybridization $T_m$ values with CYP21A1P, RAP1GA1 and DUX2 (and all other non-target genes) ~5-10° C. All cross-hybridizations at assay temperature 80° C. are expected to disappear.

TABLE 2

Calculated hybridization properties between oligo probes and target/non-target genes within the test database

| Oligo probes | Probe 1 Hybridization Tm (° C.) | Probe 1 Hybridization percentage[a] (%) | Probe 2 Hybridization Tm (° C.) | Probe 2 Hybridization percentage[a] (%) |
|---|---|---|---|---|
| Target gene: CYP21A2 | 93 | 100 | 86 | 100 |
| Non-target genes: | | | | |
| CYP21A1P | 82 | 69 | 73[b] | 4[b] |
| RAP1GA1 | 79 | 39 | 74[b] | 6[b] |
| DUX2 | 80 | 46 | 74[b] | |

Probe 1: (SEQ ID NO 2) CAGGCCATAGAGAAGAGGGATCA-CATCGTGGAGATGCAGCTGAGGCAGCACAA-GGAGAGC;
Probe 2: (SEQ ID NO 3) CAGGCCATAGAGAAGAcGGATCACATCGTtGAGATGCAGCTGAGt-CAGCA-CAAGGAGAGC. Bold letters are the mutation sites; lower case letters represent mutation sequences.
[a]Hybridization percentage of target-probe dimer among all possible states (monomer, homodimer and heterodimer) in equilibrium at 80° C.
[b]Expected not to contribute to cross-hybridization at assay temperature.

Nearest neighbor $T_m$ calculations, especially using OMP, showed an excellent linear correlation with experimental $T_d$ for single-mismatched pairs, even though it was difficult to set the right salt and oligonucleotide concentration parameters. $T_m$ of 50mer oligonucleotides with 80 and 74% sequence similarity were calculated. Their hybridization condition was under 42° C. and our $T_m$ calculation at 150 mM salt and 100 pM oligo concentration (rough estimate) for an 80% similarity pair was 47° C., while that for a 74% similarity pair was 24° C. It is tempting to say that an 80% similarity pair has a chance for hybridization while a 74% similarity one does not, as indicated by the experimental results. However, the oligo concentration was increased at 100 nM, the calculated $T_m$ values of 80 and 74% similarity pairs were 67 and 52° C., respectively. The dependable interpretation should be that calculated $T_m$ of an 80% similarity pair of that specific sequence arrangement differs from that of a 74% similarity pair large enough to be easily distinguishable in the hybridization experiments. Since our purpose is to find the guidelines for introducing mismatch pairs to distinguish two similar sequences, the relative $T_m$ values at fixed parameter conditions is all that is needed. Absolute calculated $T_m$ can be adjusted according to each experimental condition. Even though all nearest neighbor parameters were obtained from oligos <20mers, an experimental study reported that single base mismatch results from long DNA (373 bp) agreed well with published studies of short oligos, and Mfold server, one of the commonly-used oligonucleotide hybridization web services using nearest neighbor parameters (http://www.bioinfo.rpi.edu/applications/mfold/), recommends that results from oligo lengths <100 bp are reliable.

If hybridization $T_m$ of longer oligos is higher because of the additive nature of enthalpy and entropy changes in calculation, the effect of one point mutation on the $T_m$ will be smaller in longer oligos. FIG. 8B quantitatively describes the change of $T_m$ by single point mutation in relation to length. Surprisingly, calculated $T_m$ differences by point mutation do not depend on the original mRNA's GC content. There is also little dependency of $\Delta T_m$ on the oligo probe's GC content (data not shown). Statistical data shows that one point mutation of oligo 60mer does not change $|\Delta T_m|$ much, while that of oligo 20mer can significantly change $|\Delta T_m|$. This is key data in support of matched sequences with non-target genes from a similarity test as candidates for mutations. For long oligo of 50mer or 60mer, the perfect 50 or 60 consecutively match sequences are searched. Even if the sequence similarity test finds 20 consecutive sequence matches with other genes, one point mutation can dramatically reduce the hybridization $T_m$ with non-target genes, while maintaining a similar $T_m$ for the target gene. However, the large standard deviation of $|\Delta T_m|$ especially in shorter oligos, raises the following issues.

FIG. 9 provides crucial guidelines for increasing $|\Delta T_m|$ using a single-point mutation in terms of a single nucleotide and its position, which are the most relevant indicators to probe design. The 5' and 3' directions are out of the guidelines based on analysis of the data. Published experimental data asserts that a maximum destabilizing effect of a mismatch can be obtained at the center of an oligo. However, our data indicates that the position of the mutation is less significant than the identity of the nucleotides involved in the mutation, excluding the three positions at either end of the oligo. Mutating a G at position 5 will, on average, produce a significantly greater $\Delta T_m$ than a mutation from A or T to G at position 10, which is at the center of an oligo 20mer. This follows from the nature of nearest neighbor calculation except that more position dependency was shown near the oligo terminals than predicted by the nearest neighbor calculation. FIG. 9D, adapted from experimental data in Urakawa et al. and displayed in a different shading and shape for each sequential change, clearly supports our assertion. Interestingly, the 11th positions from the 5'-end of both oligo1 and oligo2 were G. Without considering the sequences, position 11 from the 5'-end can be misinterpreted as a critical position for mutations. However, our study is limited to properties in solution. There is a prior art report of microarray signal dependency on mismatch position of the 60mer oligos attached on the surface. Even though sequence effects were not considered and it was not clear how many genes were used for the mismatch position experiments, there seem to be distinctive differences between positions close to the surface and away from the surface. Note that the $T_d$ measurement experiments were also done on the surface-attached oligos (about 20mers) and agreed very well with the calculations in relative terms. Surface effects seem to be more important as oligo length increases, which is beyond the scope of this paper.

For each sequence, the following changes are suggested to produce the greatest $\Delta T_m$: A to T, T to A, C to T and G to T. G to T has the best change because the standard deviation is much smaller, even though the mean $\Delta T_m$ value of G to C is larger (FIG. 9C). Similarly, mutations from T to A have a smaller standard deviation than T to C, which is obvious in oligo lengths 30mer and longer. Summarizing the results from single-point mutation, the design guidelines for the mutated probes are as follows: (i) find the sequence similarity area with other non-target genes; (ii) exclude the last three end positions; (iii) search for a G mutation; and (iv) avoid mutations from A to G or T to G.

Among the sequence changes in FIG. 9, A to G and T to G show significantly smaller $|\Delta T_m|$ than others, while G to T and G to C show significantly larger $|\Delta T_m|$ than most others. Mutation from A to G leads to [G, T] mismatches, which are among those most commonly observed in DNA. Thermodynamic studies of [G, T] mismatches have shown them to be stable duplexes. Similarly, mismatches [G, A] resulting from mutation T to G have also been reported as stable duplexes. On the other hand, G to T mutation leads to [C, T] mismatches that various thermodynamic studies report as one of the most unstable pairs. Mismatches [C, C] due to G to C mutations have also been reported to significantly destabilize the duplexes. Our in silico results correlate well with previous experimental findings.

Figure 11:
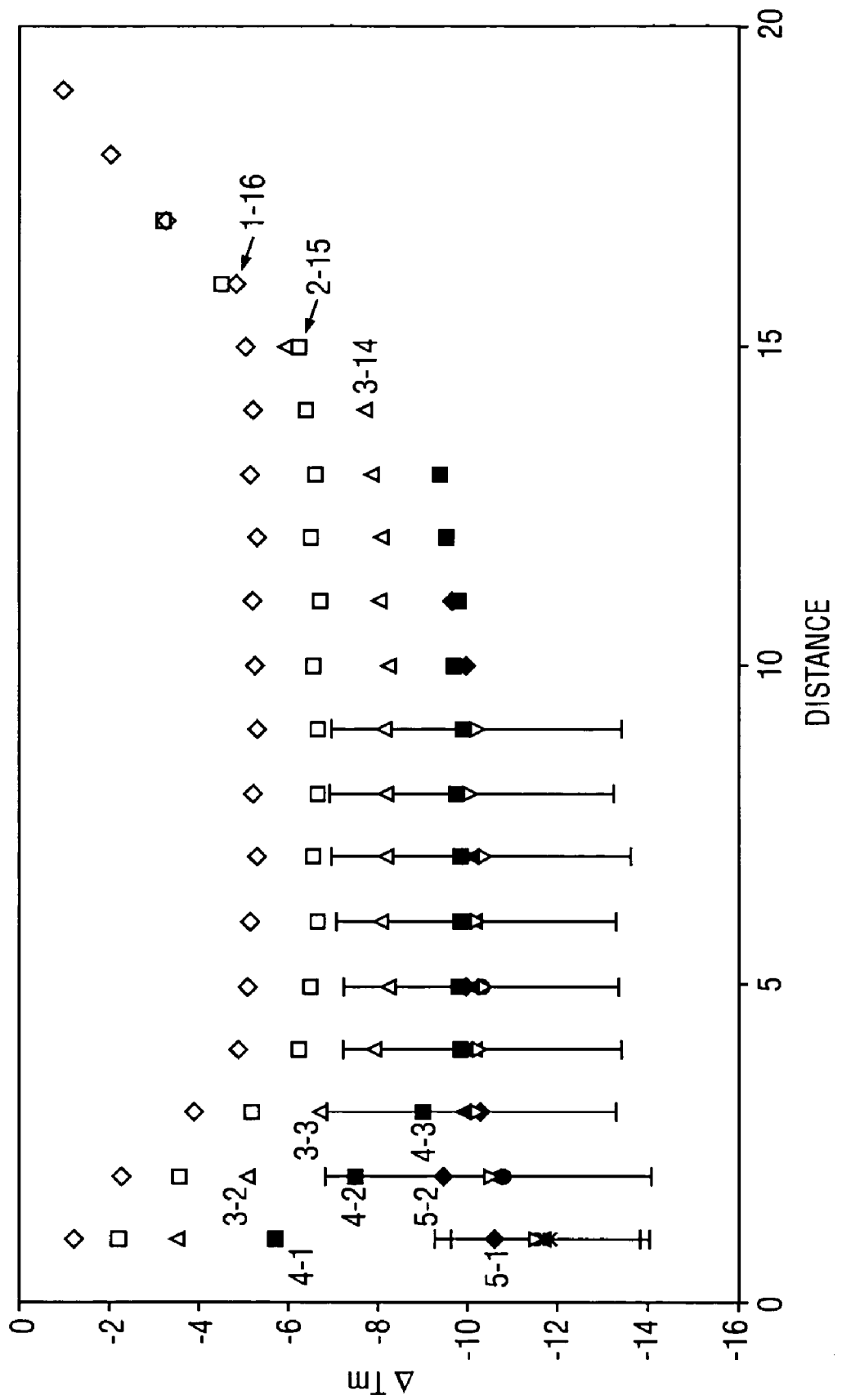
FIG. 11 provides plots of the calculated $\Delta Tm$ dependency on the reference position and the distance between two mutation sites by two-point mutations of 20mer oligonucleotide. Open diamonds represent reference position 1, open squares reference position 2, open triangle position 3, filled squares position 4, filled diamonds position 5, open inverted triangles position 6, filled triangles position 7, filled circles position 8, filled inverted triangles position 9, and X position 10. Only reference positions 6 and 10 display standard deviations. Certain reference position and distances, explained in the main text, are annotated.

When two mutation sites are introduced into oligo pairs, much larger $|\Delta T_m|$ can be achieved than with single-point mutations with stronger length dependency. This implies that careful selection of mutation sites will allow us to distinguish between two similar genes. FIG. 11 provides a concise guideline for this selection. Once the cases which will produce a large $|\Delta T_m|$ using two-point mutations are selected from FIG. 11, an important factor in achieving the greatest $T_m$ change is to consider specific nucleotides such as including mutations from G. Additional information regarding the relation between distance and specific nucleotides can be obtained from FIG. 12. Although a trend of distances 1 and 2 producing the largest $|\Delta T_m|$ values in FIG. 11, FIG. 12 demonstrates that specific nucleotide mutations have a significant effect. When both mutations are from G, next nearest neighbor pairs will provide the largest $T_m$ change. Nearest neighbor mutation pairs provide the greatest $|\Delta T_m|$ in all other cases, excluding the C to T, C to T pairs.

Our approach to using strategic point mutations for increased oligo probe specificity could greatly improve microarray results, particularly with gene families that present probe design challenges. We have identified guidelines for the introduction of point mutations in probe design. Using P450 CYP21A2, we demonstrate that application of the point mutation guidelines can improve probe specificity in the challenging case where significant sequence similarity exists between the target gene and non-target genes. An additional benefit in regard to mismatch pair probes is that we could reduce target-probe hybridization $T_m$ if the experimental preference is for a narrower $T_m$ range, such as around 85° C. in the example of Table 2. Calculating the $\Delta T_m$ for all possible mutation pairs for all potential probes of a target gene is impractical due to the exponential growth of the number of probes as the length of a target gene increases. Therefore, practical guidelines are presented for point mutation selections that require little computational overhead. In addition to improving probe specificity among gene family members, this approach promises to improve the design of oligo probes for SNP detection. There are several points to be considered, however. All these calculations are based on solution equilibrium, while microarray probes are on a solid platform. Surface effects need to be added. Secondly, all calculations are hybridization of two oligos, not of a gene and an oligo, or multiple genes and an oligo. Current computational models cannot deal with these factors. Finally, our results and guidelines are based on theoretical modeling; therefore, laboratory validation is imperative, even though independent experimental data have already proved the value of our guidelines for single-point mutations.

Calculating Target-Specific Hybridization Sequences Determined by the Method of the Invention.

With reference to Table 3, a collection of potential probes designed by the method of the invention are provided. These probes were designed by evaluation of mRNA sequences from the human genome which were downloaded from NCBI RefSeq site. Interfering genes were searched in the whole human RefSeq sequences.

TABLE 3

Examples of obtained probe sequences from second complementary sequences

| Accession number | Gene name | Probe sequence |
|---|---|---|
| NM_031200.1 | Homo sapiens chemokine (C-C motif) receptor 9 (CCR9), transcript variant A, mRNA | (SEQ ID NO 4) CACAGAGCACGCTTGCATCTGACTGACCC ACCATTACACCCACAGACTTCACAAGCCCTA |
| NM_005704.2 | Homo sapiens protein tyrosine phosphatase, receptor type, U (PTPRU), transcript variant 3, mRNA | (SEQ ID NO 5) CATCCGCAAAGGGAGAGACCACTATGCCTACT CCTACTACCCGAAACCGGTGAACATGAC |
| NM_016408.2 | Homo sapiens CDK5 regulatory subunit associated protein 1 (CDK5RAP1), transcript variant 1, mRNA | (SEQ ID NO 6) CTGTGGGCTGTTTAGTGCCATGCACCCTT TACAGTGTGTCCTCCAATGCAGAGGTCTCT |
| NM_015981.2 | Homo sapiens calcium/calmodulin-dependent protein kinase (CaM kinase) II alpha (CAMK2A), transcript variant 1, mRNA | (SEQ ID NO 7) GCGATGGTGTGAAGAAAAGAAAGTCCATT TCCAGCGTTCAGTTAATGGAATCCTCAGAGA |
| NM_016512.2 | Homo sapiens sperm associated antigen 11 (SPAG11), transcript variant A, mRNA | (SEQ ID NO 8) GTGGGATACTAGCGTGTCCACATTGTCC TTTGATAATGAGAAGTCATCCTCGAGCACAGC |
| NM_005569.2 | Homo sapiens LIM domain kinase 2 (LIMK2), transcript variant 2a, mRNA | (SEQ ID NO 9) TATGGTACAGGACTGTCAACGAAACCTA GCACGGCTCTTGCTTCCGGTCTTCAGAATGCC |
| NM_016733.1 | Homo sapiens LIM domain kinase 2 (LIMK2), transcript variant 2b, mRNA | (SEQ ID NO 10) CTCAAGAATCCCAGTGTGTGTGTAGCCT CCACAGAAAGGTCGTTTTCTCGGGTCCAGAG |
| NM_052934.2 | Homo sapiens solute carrier family 26, member 9 (SLC26A9), transcript variant 1, mRNA | (SEQ ID NO 11) TCCTCATACTGCCTACAGAGTGCCTAGCA CTTGGGACTTCCATAAAGGATGAGCCTGGGG |
| NM_020480.1 | Homo sapiens ankyrin 1, erythrocytic (ANK1), transcript variant 7, mRNA | (SEQ ID NO 12) GACGAGGAGACTATCTCACCCAGGGTGG TCCGACGGCGGGTCTTCCTGAAGCGGAATGAG |
| NM_030380.1 | Homo sapiens GLI-Kruppel family member GLI2 (GLI2), transcript variant 2, mRNA | (SEQ ID NO 13) CCCGTACCACAGCATGCTCTACTACTACGG CCAAATCCACATATACGAACAGGATGGAGG |

TABLE 4

Nearest neighbor parameters for oligonucleotides in 1M NaCl

| Sequence | $\Delta H$ (kcal/mol) | $\Delta S$ (cal/k · mol) | $\Delta G_{37}$ (kcal/mol) | reference |
|---|---|---|---|---|
| AA/TT | −7.9 | −22.2 | −1[1] | (1) |
| AT/TA | −7.2 | −20.4 | −0.88[1] | (1) |
| TA/AT | −7.2 | −21.3 | −0.58[1] | (1) |
| CA/GT | −8.5 | −22.7 | −1.45[1] | (1) |
| GT/CA | −8.4 | −22.4 | −1.44[1] | (1) |
| CT/GA | −7.8 | −21 | −1.28[1] | (1) |
| GA/CT | −8.2 | −22.2 | −1.3[1] | (1) |
| CG/GC | −10.6 | −27.2 | −2.17[1] | (1) |
| GC/CG | −9.8 | −28.2 | −2.24[1] | (1) |
| GG/CC | −8 | −19.9 | −1.84[1] | (1) |
| AA/TA | 1.2 | 1.91 | 0.61 | (2) |
| CA/GA | −0.9 | −4.29 | 0.43 | (2) |
| GA/CA | −2.9 | −9.9 | 0.17 | (2) |
| TA/AA | 4.7 | 12.93 | 0.69 | (2) |
| AC/TC | 0 | −4.29 | 1.33 | (2) |
| CC/GC | −1.5 | −7.1 | 0.7 | (2) |
| GC/CC | 3.6 | 9.07 | 0.79 | (2) |
| TC/AC | 6.1 | 16.29 | 1.05 | (2) |
| AG/TG | −3.1 | −9.58 | −0.13 | (2) |
| CG/GG | −4.9 | −15.45 | −0.11 | (2) |
| GG/CG | −6 | −15.77 | −1.11 | (2) |
| TG/AG | −1.6 | −6.58 | 0.44 | (2) |
| AT/TT | −2.7 | −10.94 | 0.69 | (2) |
| CT/GT | −5 | −15.74 | −0.12 | (2) |
| GT/CT | −2.2 | −8.55 | 0.45 | (2) |
| TT/AT | 0.2 | −1.55 | 0.68 | (2) |
| AA/TC | 2.3 | 4.6 | 0.88 | (3) |
| AC/TA | 5.3 | 14.6 | 0.77 | (3) |
| CA/GC | 1.9 | 3.7 | 0.75 | (3) |
| CC/GA | 0.6 | −0.6 | 0.79 | (3) |
| GA/CC | 5.2 | 14.2 | 0.81 | (3) |
| GC/CA | −0.7 | −3.8 | 0.47 | (3) |
| TA/AC | 3.4 | 8 | 0.92 | (3) |
| TC/AA | 7.6 | 20.2 | 1.33 | (3) |
| AC/TT | 0.7 | 0.2 | 0.64 | (4) |
| AT/TC | −1.2 | −6.2 | 0.73 | (4) |
| CC/GT | −0.8 | −4.5 | 0.62 | (4) |
| CT/GC | −1.5 | −6.1 | 0.4 | (4) |
| GC/CT | 2.3 | 5.4 | 0.62 | (4) |
| GT/CC | 5.2 | 13.5 | 0.98 | (4) |
| TC/AT | 1.2 | 0.7 | 0.97 | (4) |
| TT/AC | 1 | 0.7 | 0.75 | (4) |
| AA/TG | −0.6 | −2.3 | 0.14 | (5) |
| AG/TA | −0.7 | −2.3 | 0.02 | (5) |
| CA/GG | −0.7 | −2.3 | 0.03 | (5) |
| CG/GA | −4 | −13.2 | 0.11 | (5) |
| GA/CG | −0.6 | −1 | −0.25 | (5) |
| GG/CA | 0.5 | 3.2 | −0.52 | (5) |
| TA/AG | 0.7 | 0.7 | 0.42 | (5) |
| TG/AA | 3 | 7.4 | 0.74 | (5) |
| AG/TT | 1 | 0.9 | 0.71 | (6) |
| AT/TG | −2.5 | −8.3 | 0.07 | (6) |
| CG/GT | −4.1 | −11.7 | −0.47 | (6) |
| AT/GG | −2.8 | −8 | −0.32 | (6) |
| GG/CT | 3.3 | 10.4 | 0.08 | (6) |
| GG/TT | 5.8 | 16.3 | 0.74 | (6) |
| GT/CG | −4.4 | −12.3 | −0.59 | (6) |
| GT/TG | 4.1 | 9.5 | 1.15 | (6) |
| TG/AT | −0.1 | −1.7 | 0.43 | (6) |
| TG/GT | −1.4 | −6.2 | 0.52 | (6) |
| TT/AG | −1.3 | −5.3 | 0.34 | (6) |
| Initiate w/ | 0.1 | −2.8 | 0.98[1] | (1) |
| Initiate w/ | 2.3 | 4.1 | 1.03[1] | (1) |
| Symmetric | 0 | −1.4 | 0.4[1] | (1) |

[1]Calculated from $\Delta G°_T = \Delta H° - T\Delta S°$.

References for the supplemental material (1). SantaLucia, J., Jr. (1998) A unified view of polymer, dumbbell, and oligonucleotide DNA nearest-neighbor thermodynamics. Proc. Natl. Acad. Sci. USA, 95, 1460–1465.
(2). Peyret, N., Seneviratne, P. A., Allawi, H. T. and SantaLucia, J., Jr. (1999) Nearest-neighbor thermodynamics and NMR of DNA sequences with internal A.A, C.C, G.G, and T.T mismatches. Biochemistry, 38, 3468–3477.
(3). Allawi, H. T. and SantaLucia, J., Jr. (1998) Nearest-neighbor thermodynamics of internal A.C mismatches in DNA: sequence dependence and pH effects. Biochemistry, 37, 9435–9444.
(4). Allawi, H. T. and SantaLucia, J., Jr. (1998) Thermodynamics of internal C.T mismatches in DNA. Nucl. Acids Res., 26, 2694–2701.
(5). Allawi, H. T. and SantaLucia, J., Jr. (1998) Nearest neighbor thermodynamic parameters for internal G.A mismatches in DNA. Biochemistry, 37, 2170–2179.
(6). Allawi, H. T. and SantaLucia, J., Jr. (1997) Thermodynamics and NMR of internal G.T mismatches in DNA. Biochemistry, 36, 10581–10594.

While embodiments of the invention have been illustrated and described, it is not intended that these embodiments illustrate and describe all possible forms of the invention. Rather, the

What is claimed is:

1. A method of making a hybridization probe the method comprising: receiving a target-specific hybridization sequence identified by:
   a) selecting a candidate target nucleotide sequence in a subject nucleotide sequence;
   b) identifying one or more interfering nucleotide sequences, wherein the interfering nucleotide sequences have at least a predetermined number of sequential nucleotides in common with the candidate target nucleotide sequence;
   c) identifying a first complementary nucleotide sequence to the target nucleotide sequence;
   d) determining a set of replacement positions $P_n$ in the first complementary nucleotide sequence by locating each position at which a G is located;
   e) creating a set of second complementary nucleotide sequences by replacing each G at the replacement position with a nucleotide selected from the group consisting of T/U, C, and A, wherein each member of the set of second complementary nucleotide sequences has a single G replaced;
   f) characterizing the amount of "target-second complementary nucleotide sequence" hybrid formed when the target and second complementary nucleotide sequences are combined in the presence of potentially interfering sequences;
   g) identifying the second complementary nucleotide sequence as a symbolic representation of a target-specific hybridization sequence if the amount of "target-second complementary nucleotide sequence" hybrid is greater than a predetermined value;
   h) determining a set of replacement positions $P_n$ in the first complementary nucleotide sequence by locating each position at which a C or A or T/U if the first complementary nucleotide sequence did not have a G or the amount of "target-second complementary nucleotide sequence" hybrid was not greater than the predetermined value;
   i) creating the set of second complementary nucleotide sequences by replacing C or A or T/U identified in step h) at the replacement position with a non-complementary nucleotide;
   j) characterizing the amount of "target-second complementary nucleotide sequence" hybrid formed when the target and second complementary nucleotide sequences are combined in the presence of potentially interfering sequences; and
   k) identifying the second complementary nucleotide sequence as the symbolic representation of a target specific hybridization sequence if the amount of "target-second complementary nucleotide sequence" hybrid is greater than a predetermined value, and generating an actual nucleotide sequence that is incorporated in the hybridization probe.

2. The method of claim 1 wherein the subject nucleotide sequence has a length equal to or greater than the candidate target nucleotide sequence.

3. The method of claim 1 wherein the candidate target nucleotide sequence and the second complementary nucleotide sequence are not self complementary.

4. The method of claim 1 wherein the step of selecting the candidate target nucleotide sequence comprises: selecting an initial starting position from an end in the subject nucleotide sequence; identifying a set of candidate target sequences beginning at a set of starting positions given by the formula Xo+nA that include a predetermined number of nucleotides, wherein Xo is the initial starting position, n is an integer greater than or equal to 0 and is limited so that no sequence extends past the end of the test sequence, and A is an offset number of nucleotides between adjacent members in the set of candidate sequences; quantifying the amount of interfering sequences for each member in the set of candidate target sequences; and arranging the set of candidate target sequences from a sequence with the least amount of interfering sequences to a sequence with the greatest amount of interfering sequences.

5. The method of claim 4 wherein steps a through k are recursively executed with a different selected member from the set of candidate target sequences until a predetermined number of target-specific hybridization sequences are identified, the selected member first being sequentially selected from the member of the set with the least amount of interfering sequences to the member with the greatest amount of interfering sequences.

6. The method of claim 5 wherein A is from 1 to 50 nucleotides in length, and each member in the set of candidate sequences has from about 15 to about 100 nucleotides.

7. The method of claim 6 wherein Xo is at a position from the first position to about the 1500$^{th}$ position in the subject nucleotide sequence.

8. The method of claim 1 wherein the target nucleotide sequence is selected by: choosing a sequence from the collection of nucleotide sequences; identifying a nucleotide at a predetermined position from an end of the sequence; and selecting as the candidate target nucleotide sequence a nucleotide sequence starting at the predetermined position that includes a predetermined number of nucleotides.

9. The method of claim 1 further comprising: determining a replacement position in the first complementary nucleotide sequence at which a C is located, wherein a predetermined number of nucleotides from each end of the subject nucleotide sequence are excluded from consideration when determining the replacement position; and creating the second complementary nucleotide sequences by replacing the C at the replacement position with a nucleotide selected from the group consisting of T/U, G, and A.

10. The method of claim 1 further comprising: determining a replacement position in the first complementary nucleotide sequence at which an A is located, wherein a predetermined number of nucleotides from each end of the subject nucleotide sequence are excluded from consideration when determining the replacement position; and creating the second complementary nucleotide sequences by replacing the A at the replacement position with a nucleotide selected from the group consisting of T/U and C.

11. The method of claim 1 further comprising: determining a replacement position in the first complementary nucleotide sequence at which a T/U is located, wherein a predetermined number of nucleotides from each end of the subject nucleotide sequence are excluded from consideration when determining the replacement position; and creating the second complementary nucleotide sequences by replacing the T/U at the replacement position with a nucleotide selected from the group consisting of A and C.

12. The method of claim 1 further comprising: prior to step f, identifying one or more interfering nucleotide sequences, wherein the interfering nucleotide sequences have at least a predetermined number of sequential nucleotides in common with the second complementary nucleotide sequence.

13. The method of claim 12 wherein the interfering nucleotide sequences have at least 14 sequential nucleotides in common with the target complementary nucleotide sequence.

14. The method of claim 12 wherein the step of characterizing the amount of the "target-second complementary nucleotide sequence" hybrid comprises:
calculating the differences between a hybridization function for a "target-second complementary nucleotide sequence" hybrid and an "interfering sequences-second complementary nucleotide sequence" hybrid, the hybridization function providing quantification of the amount of hybridization; and step g comprises: if the differences are such that the amount of the "target-second complementary nucleotide sequence" hybrid is greater than the predetermined value, identifying the second complementary nucleotide sequence as the target-specific hybridization sequence.

15. The method of claim 14 wherein the hybridization function is the melt temperature, the difference in Gibbs free energy, interaction energy, or the percent hybridization.

16. The method of claim 1 further comprising:
l) if the first complementary nucleotide sequence did not have a G or the differences were not greater than the predetermined value, determining a set of replacement positions $P_n$ in the first complementary nucleotide sequence by locating each position at which a C is located;
m) creating the set of second complementary nucleotide sequences by replacing each C at the replacement position with a nucleotide selected from the group consisting of T/U, G, and A, wherein each member of the set of second complementary nucleotide sequences has a single C replaced;
n) characterizing the amount of "target-second complementary nucleotide sequence" hybrid formed when the target and second complementary nucleotide sequences are combined in the presence of potentially interfering sequences; and
o) if the amount of "target-second complementary nucleotide sequence" hybrid is greater than a predetermined value, identifying the second complementary nucleotide sequence as the symbolic representation of a target specific hybridization sequence.

17. The method of claim 16 further comprising:
p) if the first complementary nucleotide sequence did not have a C or the differences were not greater than the predetermined value, determining a set of replacement positions $P_n$ in the first complementary nucleotide sequence by locating each position at which a A or T/U is located;
q) creating the set of second complementary nucleotide sequences by replacing each A at the replacement position with a nucleotide selected from the group consisting of T/U and C or by replacing each T/U at the replacement position with a nucleotide selected from the group consisting of A and C, wherein each member of the set of second complementary nucleotide sequences has a single C replaced,
r) characterizing the amount of "target-second complementary nucleotide sequence" hybrid formed when the target and second complementary nucleotide sequences are combined in the presence of potentially interfering sequences; and
s) if the amount of "target-second complementary nucleotide sequence" hybrid is greater than a predetermined value, identifying the second complementary nucleotide sequence as the symbolic representation of a target specific hybridization sequence.

18. The method of claim 1 wherein steps a-g are implemented on a microprocessor.

19. The method of claim 1 wherein the mismatch is at a position exclusive of a predetermined number of nucleotides at either end of the second complementary nucleotide sequence.

* * * * *